United States Patent
Shimizu et al.

(10) Patent No.: US 11,471,382 B2
(45) Date of Patent: Oct. 18, 2022

(54) EMULSION WITH MATTE EFFECTS AND EXCELLENT TEXTURE

(71) Applicant: L'OREAL, Paris (FR)

(72) Inventors: Momoko Shimizu, Tokyo (JP); Rui Niimi, Kanagawa (JP); Romain Tachon, Tokyo (JP); Ritesh Sinha, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/302,905

(22) PCT Filed: Jul. 18, 2017

(86) PCT No.: PCT/JP2017/026589
§ 371 (c)(1),
(2) Date: Nov. 19, 2018

(87) PCT Pub. No.: WO2018/021202
PCT Pub. Date: Feb. 1, 2018

(65) Prior Publication Data
US 2019/0290557 A1  Sep. 26, 2019

(30) Foreign Application Priority Data
Jul. 26, 2016 (JP) ............... JP2016-146095

(51) Int. Cl.
| | | |
|---|---|---|
| A61K 8/06 | (2006.01) | |
| A61K 8/85 | (2006.01) | |
| A61Q 1/00 | (2006.01) | |
| A61K 8/02 | (2006.01) | |
| A61K 8/73 | (2006.01) | |
| A61K 8/92 | (2006.01) | |

(52) U.S. Cl.
CPC .............. *A61K 8/06* (2013.01); *A61K 8/0279* (2013.01); *A61K 8/731* (2013.01); *A61K 8/85* (2013.01); *A61K 8/92* (2013.01); *A61Q 1/00* (2013.01); *A61K 2800/412* (2013.01); *A61K 2800/48* (2013.01); *A61K 2800/524* (2013.01)

(58) Field of Classification Search
None
See application file for complete search history.

(56) References Cited

U.S. PATENT DOCUMENTS

2014/0370062 A1  12/2014  Fageon et al.
2018/0116947 A1*  5/2018  Scotland ............... A61K 8/064

FOREIGN PATENT DOCUMENTS

| BR | 102012020901-2 A2 | 6/2014 | |
|---|---|---|---|
| BR | 102012020901 A2 * | 6/2014 | |
| DE | 102013209894 A1 | 12/2014 | |
| EP | 2660272 A1 * | 11/2013 | ............... C08J 3/14 |
| EP | 2660272 A1 | 11/2013 | |
| EP | 2774598 A1 | 9/2014 | |
| JP | 2004-529173 A | 9/2004 | |
| JP | 5110225 B | 12/2012 | |
| JP | 2016-518426 A | 6/2016 | |
| WO | 02/092046 A1 | 11/2002 | |
| WO | 2012/105140 A1 | 8/2012 | |
| WO | 2013/190102 A2 | 12/2013 | |
| WO | 2014/184228 A1 | 11/2014 | |
| WO | 2017/195800 A1 | 11/2017 | |

OTHER PUBLICATIONS

Toraypearl®, available at https://www.toray.jp/chemical/en/polymer/pdf/catalog_pol01.pdf, Copyright 2007, accessed on Oct. 24, 2020.*
International Search Report for counterpart Application No. PCT/JP2017/026589, dated Oct. 16, 2017.
Office Action for counterpart European Application No. 17751857.8, dated Feb. 20, 2020.
Translated Japanese Office Action for counterpart Application No. 2016-146095, dated May 25, 2020.

* cited by examiner

*Primary Examiner* — H. Sarah Park
(74) *Attorney, Agent, or Firm* — The Marbury Law Group, PLLC

(57) ABSTRACT

The present invention relates to a composition in the form of an emulsion, comprising: (a) at least one oil-absorbable organic particle which has an oil-absorbing capacity of 170 ml/100 g or more, preferably 250 ml/100 g or more, and more preferably 400 ml/100 g or more, and a volume-average particle size of less than 30 μm, preferably less than 25 μm, and more preferably less than 20 μm, (b) at least one oil; (c) at least one emulsifier; (d) water; and (e) optionally at least one additional oil-absorbable particle, wherein the oil-absorbing capacity of the total of the (a) oil-absorbable organic particle and the (e) additional oil-absorbable particle in the composition is more than 170 ml/100. The composition according to the present invention can provide long-lasting matte effects, while imparting excellent texture.

20 Claims, No Drawings

EMULSION WITH MATTE EFFECTS AND EXCELLENT TEXTURE

CROSS REFERENCE TO RELATED APPLICATIONS

This is a national stage application of PCT/JP2017/026589, filed internationally on Jul. 18, 2017, which claims priority to Japanese Application No. 2016-146095, filed on Jul. 26, 2016, both of which are incorporated by reference herein in their entireties.

TECHNICAL FIELD

The present invention relates to a composition in the form of an emulsion including at least one specific oil-absorbable organic particle, in particular a cosmetic composition for the skin, as well as a cosmetic method using the same.

BACKGROUND ART

It has been known that shiny or greasy skin due to sebum may emphasize the roughness on the skin. In other words, shiny skin may make skin roughness such as pores and wrinkles more noticeable. Therefore, users of cosmetic products would like to achieve a matte appearance of the skin.

There are some oil-absorbable powders. Such powders may be used in cosmetic products to provide the skin with immediate matte effects by absorbing sebum with these powders.

However, the above powders may not have sufficient oil-absorption capacity. Thus, the immediate matte effects may not last for a long period of time.

The lastingness of immediate matte effects which can prevent skin from being shiny or greasy is important as a cosmetic performance. Especially, maintaining matte effects provided by cosmetic products during the day is required in, in particular, hot and humid countries.

Hard resins or polymers may be used for maintaining immediate matte effects. However, they tend to impart stickiness or a less smooth texture to the skin.

For cosmetic products which can be applied onto the skin, it is required to impart a good texture resulting, for example, in smooth application and good spreadability after application. Thus, stickiness or a less smooth texture should be reduced or avoided.

In addition, it should be noted that if oil-absorbable powders are used in cosmetic products, they may impart a squeaky texture due to the contact of the powder particles.

Accordingly, there has been a need for cosmetic products which can provide long-lasting matte effects, while imparting excellent texture resulting, for example, in smooth application.

JP-B-5110225 (TORAY) discloses a specific oil-absorbable powder. However, JP-B-5110225 does not focus on the lastingness of matte effects, while imparting excellent texture.

DISCLOSURE OF INVENTION

An objective of the present invention is to provide a composition which can provide long-lasting matte effects, while imparting excellent texture, and therefore, is useful for cosmetic products.

The above objective can be achieved by a composition in the form of an emulsion, comprising:

(a) at least one oil-absorbable organic particle which has an oil-absorbing capacity of 180 ml/100 g or more, preferably 250 ml/100 g or more, and more preferably 400 ml/100 g or more, and a volume-average particle size of less than 30 μm, preferably less than 25 μm, more preferably less than 20 μm, and even more preferably from 8 to less than 12 μm;

(b) at least one oil;

(c) at least one emulsifier;

(d) water; and (e) optionally at least one additional oil-absorbable particle, wherein the oil-absorbing capacity of the total of the (a) oil-absorbable organic particle and the (e) additional oil-absorbable particle in the composition is more than 170 ml/100 g.

It is preferable that the (a) oil-absorbable organic particle be porous.

It is preferable that the (a) oil-absorbable organic particle comprise at least one organic material derived from plants.

It is preferable that the (a) oil-absorbable organic particle comprise at least one organic material selected from the group consisting of polylactic acids, celluloses, and mixtures thereof.

The amount of the (a) oil-absorbable organic particle in the composition may be from 0.01 to 30% by weight, preferably from 0.1 to 20% by weight, and more preferably from 1 to 10% by weight, relative to the total weight of the composition.

The amount of the (b) oil in the composition may be from 1 to 99% by weight, preferably from 10 to 90% by weight, and more preferably from 20 to 80% by weight, relative to the total weight of the composition.

The amount of the (c) emulsifier in the composition may be from 0.01 to 20% by weight, preferably from 0.05 to 15% by weight, and more preferably from 0.1 to 10% by weight, relative to the total weight of the composition.

The amount of the (d) water in the composition may be from 1 to 99% by weight, preferably from 10 to 90% by weight, and more preferably from 20 to 80% by weight, relative to the total weight of the composition.

The (e) additional oil-absorbable particle may comprise at least one material selected from the group consisting of cellulose, silica, silicate, perlite, boron nitride, magnesium carbonate, magnesium hydroxide, hydrophobic silica such as silica silicate, kaolin, talc, polyamide (in particular Nylon-6) powders, powders of acrylic polymers, especially of polymethyl methacrylate, of polymethyl methacrylate/ethylene glycol dimethacrylate, of polyallyl methacrylate/ethylene glycol dimethacrylate, or of ethylene glycol dimethacrylate/lauryl methacrylate copolymer, silicones, and mixtures thereof.

It is preferable that the (e) additional oil-absorbable particle have an oil-absorbing capacity of 140 ml/100 g or more, preferably 250 ml/100 g or more, and more preferably 400 ml/100 g or more.

It is preferable that the oil-absorbing capacity of the total of the (a) oil-absorbable organic particle and the (e) additional oil-absorbable particle in the composition be more than 200 ml/100 g, and preferably more than 250 ml/100 g.

The composition according to the present invention may further comprise at least one selected from the group consisting of polyols, thickeners, preservatives, co-preservatives, and mixtures thereof.

It is preferable that the composition be a cosmetic composition, preferably a skin cosmetic composition, and more preferably a skin makeup composition.

The present invention also relates to a cosmetic process for a keratin substance, preferably the skin, comprising applying to the keratin substance the composition according to the present invention.

BEST MODE FOR CARRYING OUT THE INVENTION

After diligent research, the inventors have discovered that it is possible to provide a composition which can provide long-lasting matte effects, while imparting excellent texture.

Thus, the composition according to the present invention is in the form of an emulsion, and comprises:

(a) at least one oil-absorbable organic particle which has an oil-absorbing capacity of 180 ml/100 g or more, preferably 250 ml/100 g or more, and more preferably 400 ml/100 g or more, and a volume-average particle size of less than 30 µm, preferably less than 25 prn, more preferably less than 20 µm and even more preferably from 8 to less than 12 µm;
(b) at least one oil;
(c) at least one emulsifier; and
(d) water; and
(e) optionally at least one additional oil-absorbable particle, wherein the oil-absorbing capacity of the total of the (a) oil-absorbable organic particle and the (e) additional oil-absorbable particle in the composition is more than 170 ml/100 g.

According to the present invention, the (a) oil-absorbable organic particle has sufficient oil-absorbing capacity, and can provide long-lasting matte effects, even though the (a) oil-absorbable organic particle is used together with the (b) oil.

Further, since the (a) oil-absorbable organic particle comprises organic material(s), the friction of the (a) oil-absorbable organic particle with the skin can be reduced as compared to an oil-absorbable inorganic particle, and therefore, the feeling to the touch on the skin can be improved by the composition according to the present invention.

Furthermore, since the particle size of the (a) oil-absorbable organic particle is limited, the oil-absorbing action by the particle can be increased and the feeling to the touch of the particle can be smooth as compared to a larger oil-absorbable particle, and therefore, the matte effects and the feeling to the touch on the skin can be improved by the composition according to the present invention.

Since the composition according to the present invention is in the form of an emulsion including the (b) oil, the (c) emulsifier, and the (d) water, the composition can impart excellent texture, even though the composition according to the present invention includes the (a) oil-absorbable organic particle. The composition according to the present invention does not provide any squeaky texture even when the amount of the (a) oil-absorbable organic particle increases.

If the composition according to the present invention further includes (e) additional oil-absorbing particle, long-lasting matte effects and excellent texture imparted by the composition according to the present invention may be furthermore improved.

Hereafter, the composition according to the present invention will be described in a detailed manner.

[Oil-Absorbable Organic Particle]

The composition according to the present invention includes at least one (a) oil-absorbable organic particle which has an oil-absorbing capacity of 180 ml/100 g or more, and a volume-average particle size of less than 30 µm.

If two or more (a) oil-absorbable organic particles are used, they may be the same or different.

The (a) oil-absorbable organic particle is capable of absorbing (and/or adsorbing) an oil or a liquid fatty substance, for instance sebum (from the skin).

It is preferable that the (a) oil-absorbable organic particle have an oil-absorbing capacity of 200 ml/100 g or more, more preferably 250 ml/100 g or more, even more preferably 300 ml/100 g or more, further more preferably 350 ml/100 g or more, even further more preferably 400 ml/100 g or more, and further still even more preferably 440 ml/100 g or more.

The (a) oil-absorbable organic particle may have an oil-absorbing capacity of 2000 ml/100 g or less, preferably 1800 ml/100 g or less, more preferably 1600 ml/100 g or less, even more preferably 1400 ml/100 g or less, further more preferably 1200 ml/100 g or less, even further more preferably 1000 ml/100 g or less, and further still even more preferably 800 ml/100 g or less.

Thus, the (a) oil-absorbable organic particle may have an oil-absorbing capacity ranging from 170 ml/100 g to 2000 ml/100 g, preferably from 200 ml/100 g to 1800 ml/100 g, more preferably from 250 ml/100 g to 1600 ml/100 g, even more preferably from 300 ml/100 g to 1400 ml/100 g, further more preferably from 350 ml/100 g to 1200 ml/100 g, even further more preferably from 400 ml/100 g to 1000 ml/100 g, and further still even more preferably from 440 ml/100 g to 800 ml/100 g.

The amount of oil absorbed (and/or adsorbed) by the (a) oil-absorbable organic particle may be characterized by measuring the wet point according to the method described below. The oil-absorbing capacity measured at the wet point, noted Wp, corresponds to the amount of oil that needs to be added to 100 g of particle in order to obtain a homogeneous paste.

The amount of the absorbed (and/or adsorbed) oil can be measured according to the method for determining the oil uptake of a powder described in standard ISO 787/5-1980. It corresponds to the amount of oil absorbed/adsorbed onto the available surface of the powder, by measuring the wet point.

An amount m (in grams) of the (a) oil-absorbable organic particle of between about 0.5 g and about 5 g (the amount depends on the density of the (a) oil-absorbable organic particle, but typically 2 g) is placed on a glass plate and isononyl isononanoate is then added dropwise.

After addition of 4 to 5 drops of purified linseed oil, the isononyl isononanoate is incorporated into the (a) oil-absorbable organic particle using a spatula, and addition of the isononyl isononanoate is continued until a conglomerate of isononyl isononanoate and powder has formed. At this point, the isononyl isononanoate is added one drop at a time and the mixture is then triturated with the spatula. The addition of isononyl isononanoate is stopped when a firm, smooth paste is obtained. This paste must be able to be spread on the glass plate without cracking or forming lumps. The volume Vs (expressed in ml) of isononyl isononanoate used is then noted.

The oil uptake corresponds to the ratio Vs/m.

In the above protocol to determine the wet point, isononyl isononanoate may be replaced with oleic acid or linseed oil. Unless otherwise defined, oil-absorbing capacities defined in the present invention mean those measured by using isononyl isononanoate.

It is preferable that the (a) oil-absorbable organic particle have a volume-average particle size of less than 25 µm, more preferably less than 20 µm, and even more preferably less than 15 µm. Unless otherwise defined, particle sizes or average particle sizes defined in the present invention mean volume-average particle sizes.

The (a) oil-absorbable organic particle may have a volume-average particle size of 1 µm or more, preferably 3 µm or more, more preferably 5 µm or more, and even more preferably 7 µm or more.

The (primary) particle size of the (a) oil-absorbable organic particle may be from 1 to 30 µm, preferably from 3 to less than 25 µm, more preferably from 5 to less than 20 µm, even more preferably from 7 to less than 15 µm, and even more preferably from 8 to less than 12 µm. The (primary) particle size can be measured by, for example, extracting and measuring from a photograph image obtained by SEM and the like, using a particle size analyzer such as a laser diffraction particle size analyzer, and the like. It is preferable to use a particle size analyzer such as a laser diffraction particle size analyzer. In this case, the (primary) particle size is the volume-average (primary) particle size.

It is preferable that the (a) oil-absorbable organic particle be a porous particle, in particular a porous spherical particle.

According to another aspect of the present disclosure, the (a) oil-absorbable organic particle may have a BET specific surface area greater than or equal to 300 $m^2/g$, for instance, greater than or equal to 500 $m^2/g$, such as greater than or equal to 600 $m^2/g$, and less than or equal to 1500 $m^2/g$.

The (a) oil-absorbable organic particle may have a density of from 0.01 to 0.9 $g/cm^3$, preferably from 0.05 to 0.5 $g/cm^3$, and more preferably from 0.1 to 0.3 $g/cm^3$.

The (a) oil-absorbable organic particle is of organic nature.

The (a) oil-absorbable organic particle comprises at least one organic material. The type of the organic material is not limited. However, it is preferable that the (a) oil-absorbable organic particle comprise at least one organic material derived from plants. In other words, it is preferable that the organic material be of plant origin.

It is preferable that the (a) oil-absorbable organic particle comprise at least one organic material selected from the group consisting of polylactic acids, celluloses, and mixtures thereof.

As preferable examples of the (a) oil-absorbable organic particle, mention may be made of polylactic acid particle sold under the name of Toraypearl® PLA (isononyl isononanoate oil uptake is 465.9 ml/100 g) with a particle size of 11 µm (porous polylactic acid) and PLA-2 (isononyl isononanoate oil uptake is 380 ml/100 g) with a particle size of 9 (porous polylactic acid, Porous block).

The amount of the (a) oil-absorbable organic particle in the composition may be from 0.01 to 30% by weight, preferably from 0.1 to 20% by weight, and more preferably from 1 to 10% by weight, relative to the total weight of the composition.

[Oil]

The composition according to the present invention comprises at least one (b) oil. If two or more (b) oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The (b) oil may be a non-polar oil such as a hydrocarbon oil, a silicone oil, or the like; a polar oil such as a plant or animal oil and an ester oil or an ether oil; or a mixture thereof.

The (b) oil may be selected from the group consisting of oils of plant or animal origin, synthetic oils, silicone oils, hydrocarbon oils, and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's Chemistry and Technology of Silicones (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

with D″: 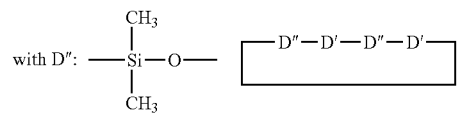

and with D″: 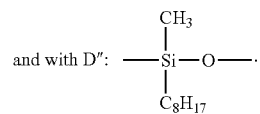

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2', 2',3,3'-hexatrimethylsilyloxy)neopentane; and (ii) linear volatile polydialkylsiloxanes containing 2 to 9 silicon atoms and having a viscosity of less than or equal to $5 \times 10^{-6}$ $m^2/s$ at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 $mm^2/s$; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

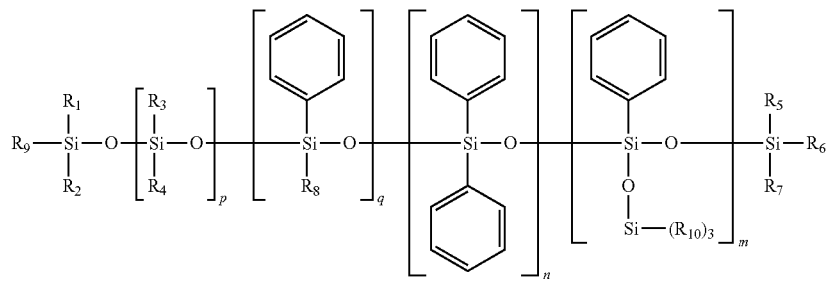

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl, or butyl radicals, and m, n, p, and q are, independently of each other, integers of 0 to 900 inclusive, preferably 0 to 500 inclusive, and more preferably 0 to 100 inclusive, with the proviso that the sum n+m+q is other than 0.

Examples that may be mentioned include the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- certain oils of the SF series from General Electric, such as SF 1023, SF 1154, SF 1250, and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:
- linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and
- linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It is preferable that the (b) oil be chosen from hydrocarbon oils, ester oils, silicone oils, and mixtures thereof.

The amount of the (b) oil in the composition according to the present invention may range from 1% to 99% by weight, preferably from 10% to 90% by weight, more preferably from 20% to 80% by weight, even more preferably from 30 to 70% by weight, and even further more preferably from 40 to 60% by weight, relative to the total weight of the composition.

The (b) oil can form a fatty phase of the composition according to the present invention.

If the composition according to the present invention is in the form of an O/W emulsion, the (b) oil in the composition according to the present invention can form dispersed fatty phases in the O/W emulsion.

If the composition according to the present invention is in the form of a W/O emulsion, the (b) oil in the composition according to the present invention can form a continuous fatty phase in the W/O emulsion.

The fatty phase may include other oily ingredients such as at least one organic UV filter.

The amount of the fatty phase in the composition according to the present invention may range from 1% to 99% by weight, preferably from 10% to 90% by weight, more preferably from 20% to 80% by weight, even more preferably from 30 to 70% by weight, and even further more preferably from 40 to 60% by weight, relative to the total weight of the composition.

[Emulsifier]

The composition according to the present invention comprises at least one (c) emulsifier. If two or more emulsifiers are used, they may be the same or different.

The amount of the (c) emulsifier(s) may be 20% by weight or less, preferably 15% by weight or less, and more preferably 10% by weight or less, relative to the total weight of the composition according to the present invention, with the proviso that the amount of the (c) emulsifier(s) is not zero. The amount of the (c) emulsifier(s) may be 0.01% by weight or more, preferably 0.05% by weight or more, and more preferably from 0.1% by weight or more, relative to the total weight of the composition.

Thus, the amount of the (c) emulsifier(s) in the composition according to the present invention may range from 0.01% to 20% by weight, preferably from 0.05% to 15% by weight, and more preferably from 0.1% to 10% by weight, relative to the total weight of the composition.

The types of the (c) emulsifier are not limited. Thus, for example, amphiphilic powder(s) may be used as the (c) emulsifier. In this case, the composition according to the present invention may be in the form of a Pickering emulsion.

It is preferable that the (c) emulsifier be selected from surfactants.

Thus, the composition according to the present invention may include at least one surfactant. Two or more surfactants may be used in combination. Thus, a single type of surfactant or a combination of different types of surfactant may be used.

The surfactant used in the present invention may be selected from the group consisting of anionic surfactants, amphoteric surfactants, cationic surfactants, and nonionic surfactants, preferably from nonionic surfactants.

(c-1) Anionic Surfactants

The composition according to the present invention may comprise at least one anionic surfactant. Two or more anionic surfactants may be used in combination.

It is preferable that the anionic surfactant be selected from the group consisting of ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates; ($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates; ($C_6$-$C_{30}$)alkyl phosphates; ($C_6$-$C_{30}$)alkyl sulfosuccinates, ($C_6$-$C_{30}$)alkyl ether sulfosuccinates, ($C_6$-$C_{30}$)alkylamide sulfosuccinates; ($C_6$-$C_{30}$)alkyl sulfoacetates; ($C_6$-$C_{24}$)acyl sarcosinates; ($C_6$-$C_{24}$)acyl glutamates; ($C_6$-$C_{30}$)alkylpolyglycoside carboxylic ethers; ($C_6$-$C_{30}$)alkylpolyglycoside sulfosuccinates; ($C_6$-$C_{30}$)alkyl sulfosuccinamates; ($C_6$-$C_{24}$) acyl isethionates; N—($C_6$-$C_{24}$)acyl taurates; $C_6$-$C_{30}$ fatty acid salts; coconut oil acid salts or hydrogenated coconut oil acid salts; ($C_8$-$C_{20}$)acyl lactylates; ($C_6$-$C_{30}$)alkyl-D-galactoside uronic acid salts; polyoxyalkylenated ($C_6$-$C_{30}$)alkyl ether carboxylic acid salts; polyoxyalkylenated ($C_6$-$C_{30}$) alkylaryl ether carboxylic acid salts; and polyoxyalkylenated ($C_6$-$C_{30}$)alkylamido ether carboxylic acid salts; and corresponding acid forms.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

It is more preferable that the anionic surfactant be selected from salts of ($C_6$-$C_{30}$)alkyl sulfate, ($C_6$-$C_{30}$)alkyl ether sulfates or polyoxyalkylenated ($C_6$-$C_{30}$)alkyl ether carboxylic acid salified or not.

(c-2) Amphoteric Surfactants

The composition according to the present invention may comprise at least one amphoteric surfactant. Two or more amphoteric surfactants may be used in combination.

The amphoteric or zwitterionic surfactants can be, for example (non-limiting list), amine derivatives such as aliphatic secondary or tertiary amine, and optionally quaternized amine derivatives, in which the aliphatic radical is a linear or branched chain including 8 to 22 carbon atoms and containing at least one water-solubilizing anionic group (for example, carboxylate, sulphonate, sulphate, phosphate, or phosphonate).

The amphoteric surfactant may preferably be selected from the group consisting of betaines and amidoaminecarboxylated derivatives.

It is preferable that the amphoteric surfactant be selected from betaine-type surfactants.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$)alkylbetaines, ($C_8$-$C_{24}$)alkylamido($C_1$-$C_8$)alkylbetaines, sulphobetaines, and ($C_8$-$C_{24}$)alkylamido($C_1$-$C_8$)alkylsulphobetaines. In one embodiment, the amphoteric surfactants of betaine type are chosen from ($C_8$-$C_{24}$)alkylbetaines, ($C_8$-$C_{24}$)alkylamido($C_1$-$C_8$)alkylsulphobetaines, sulphobetaines, and phosphobetaines.

Non-limiting examples that may be mentioned include the compounds classified in the CTFA International Cosmetic Ingredient Dictionary & Handbook, 15th Edition, 2014, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

$$R_1\text{—CONHCH}_2\text{CH}_2\text{—N}^+(R_2)(R_3)(\text{CH}_2\text{COO}^-)\text{M}^+\text{X}^- \quad \text{(B1)}$$

in which:

$R_1$ denotes an alkyl radical of an acid $R_1$—COOH present in hydrolysed coconut oil, a heptyl, nonyl, or undecyl radical, $R_2$ denotes a beta-hydroxyethyl group, $R_3$ denotes a carboxymethyl group, $M^+$ denotes a cationic ion derived from alkaline metals such as sodium; ammonium ion; or an ion derived from an organic amine;

$X^-$ denotes an organic or inorganic anionic ion such as halides, acetates, phosphates, nitrates, alkyl($C_1$-$C_4$)sulfates, alkyl ($C_1$-$C_4$)— or alkyl ($C_1$-$C_4$)aryl-sulfonates, particularly methylsulfate and ethylsulfate; or $M^+$ and $X^-$ are not present;

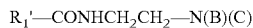  (B2)

in which:

$R_1'$ denotes an alkyl radical of an acid $R_1'$—COOH present in coconut oil or in hydrolysed linseed oil, an alkyl radical, such as a $C_7$, $C_9$, $C_{11}$, or $C_{13}$ alkyl radical, a $C_{17}$ alkyl radical and its iso-form, or an unsaturated $C_{17}$ radical, B represents —$CH_2CH_2OX'$, C represents —$(CH_2)_z$—Y', with z=1 or 2, X' denotes a —$CH_2$—COOH group, —$CH_2$—COOZ', —$CH_2CH_2$—COOH, —$CH_2CH_2$—COOZ', or a hydrogen atom, and Y' denotes —COOH, —COOZ', —$CH_2$—CHOH—$SO_3Z'$, —$CH_2$—CHOH—$SO_3H$ radical, or a —$CH_2$—CH(OH)—$SO_3$—Z' radical, wherein Z' represents an ion of an alkaline or alkaline earth metal such as sodium, an ion derived from an organic amine, or an ammonium ion;

and

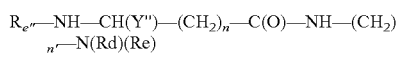  (B'2)

in which:

Y" denotes —C(O)OH, —C(O)OZ", —$CH_2$—CH(OH)—$SO_3H$ or —$CH_2$—CH(OH)—$SO_3$—Z", wherein Z" denotes a cationic ion derived from alkaline metal or alkaline-earth metals such as sodium, an ion derived from organic amine or an ammonium ion;

Rd and Re denote a $C_1$-$C_4$ alkyl or $C_1$-$C_4$ hydroxyalkyl radical;

$R_{a''}$ denotes a $C_{10}$-$C_{30}$ group alkyl or alkenyl group from an acid, and n and n' independently denote an integer from 1 to 3.

It is preferable that the amphoteric surfactant with formula B1 and B2 be selected from ($C_8$-$C_{24}$)-alkyl amphomonoacetates, ($C_8$-$C_{24}$)alkyl amphodiacetates, ($C_8$-$C_{24}$)alkyl amphomonopropionates, and ($C_8$-$C_{24}$)alkyl amphodipropionates These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid, and Cocoamphodipropionic acid.

By way of example, mention may be made of the cocoamphodiacetate sold under the trade name Miranol® C2M concentrate by the company Rhodia Chimie Among compounds of formula (B'2) mention may be made of sodium diethylaminopropyl cocoaspartamide (CTFA) marketed by CHIMEX under the denomination CHIMEXANE HB.

(c-3) Cationic Surfactants

The composition according to the present invention may comprise at least one cationic surfactant. Two or more cationic surfactants may be used in combination.

The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to:

those of general formula (B3) below:

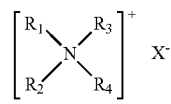  (B3)

wherein $R_1$, $R_2$, $R_3$, and $R_4$, which may be identical or different, are chosen from linear and branched aliphatic radicals including from 1 to 30 carbon atoms and optionally including heteroatoms such as oxygen, nitrogen, sulfur, and halogens. The aliphatic radicals may be chosen, for example, from alkyl, alkoxy, $C_2$-$C_6$ polyoxyalkylene, alkylamide, ($C_{12}$-$C_{22}$)alkylamido($C_2$-$C_6$)alkyl, ($C_{12}$-$C_{22}$)alkylacetate, and hydroxyalkyl radicals; and aromatic radicals such as aryl and alkylaryl; and $X^-$ is chosen from halides, phosphates, acetates, lactates, ($C_2$-$C_6$) alkyl sulfates, and alkyl- or alkylaryl-sulfonates;

quaternary ammonium salts of imidazoline, for instance those of formula (B4) below:

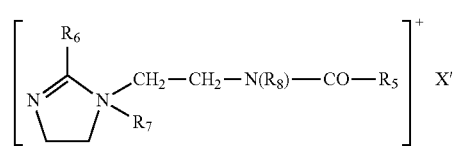  (B4)

wherein:

$R_5$ is chosen from alkenyl and alkyl radicals including from 8 to 30 carbon atoms, for example fatty acid derivatives of tallow or of coconut;

$R_6$ is chosen from hydrogen, $C_1$-$C_4$ alkyl radicals, and alkenyl and alkyl radicals including from 8 to 30 carbon atoms;

$R_7$ is chosen from $C_1$-$C_4$ alkyl radicals;

$R_8$ is chosen from hydrogen and $C_1$-$C_4$ alkyl radicals; and $X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals including from 12 to 21 carbon atoms, such as fatty acid derivatives of tallow, $R_7$ is methyl, and $R_8$ is hydrogen. Examples of such products include, but are not limited to, Quatemium-27 (CTFA 1997) and Quaternium-83 (CTFA 1997), which are sold under the names "Rewoquat®" W75, W90, W75PG and W75HPG by the company Witco;

Di or tri quaternary ammonium salts of formula (B5):

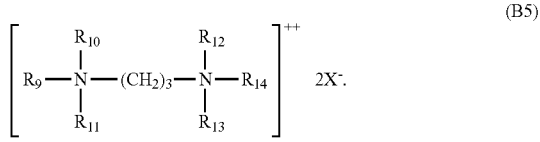

wherein:
$R_9$ is chosen from aliphatic radicals including from 16 to 30 carbon atoms;
$R_{10}$ is chosen from hydrogen or alkyl radicals including from 1 to 4 carbon atoms or a group $-(CH_2)_3(R_{16a})(R_{17a})(R_{18a})N^+X-_4$;
$R_{11}$, $R_{12}$, $R_{13}$, $R_{14}$, $R_{16a}$, $R_{17a}$, and $R_{18a}$, which may be identical or different, are chosen from hydrogen and alkyl radicals including from 1 to 4 carbon atoms; and
$X^-$ is chosen from halides, acetates, phosphates, nitrates, ethyl sulfates, and methyl sulfates.

An example of one such diquaternary ammonium salt is FINQUAT CT-P of FINETEX (Quaternium-89) or FINQUAT CT (Quaternium-75);
and
quaternary ammonium salts including at least one ester function, such as those of formula (B6) below:

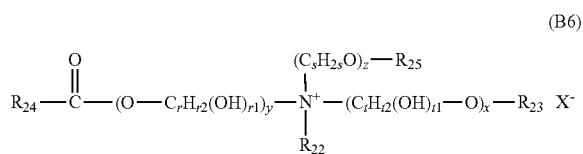

wherein:
$R_{22}$ is chosen from $C_1$-$C_6$ alkyl radicals and $C_1$-$C_6$ hydroxyalkyl and dihydroxyalkyl radicals;
$R_{23}$ is chosen from:
the radical below:

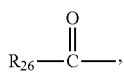

linear and branched, saturated and unsaturated $C_1$-$C_{22}$ hydrocarbon-based radicals $R_{27}$, and hydrogen,
$R_{25}$ is chosen from:
the radical below:

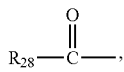

linear and branched, saturated and unsaturated $C_1$-$C_6$ hydrocarbon-based radicals $R_{29}$, and hydrogen,
$R_{24}$, $R_{26}$, and $R_{28}$, which may be identical or different, are chosen from linear and branched, saturated and unsaturated, $C_7$-$C_{21}$, hydrocarbon-based radicals;
r, s, and t, which may be identical or different, are chosen from integers ranging from 2 to 6; each of r1 and t1, which may be identical or different, is 0 or 1, and r2+r1-2r and t1+2t=2t; y is chosen from integers ranging from 1 to 10;
x and z, which may be identical or different, are chosen from integers ranging from 0 to 10;
$X^-$ is chosen from simple and complex, organic and inorganic anions; with the proviso that the sum x+y+z ranges from 1 to 15, that when x is 0, $R_{23}$ denotes $R_{27}$, and that when z is 0, $R_{25}$ denotes $R_{29}$. $R_{22}$ may be chosen from linear and branched alkyl radicals. In one embodiment, $R_{22}$ is chosen from linear alkyl radicals. In another embodiment, $R_{22}$ is chosen from methyl, ethyl, hydroxyethyl, and dihydroxypropyl radicals, for example methyl and ethyl radicals. In one embodiment, the sum x+y+z ranges from 1 to 10. When $R_{23}$ is a hydrocarbon-based radical $R_{27}$, it may be long and include from 12 to 22 carbon atoms, or short and include from 1 to 3 carbon atoms. When $R_{25}$ is a hydrocarbon-based radical $R_{29}$, it may include, for example, from 1 to 3 carbon atoms. By way of a non-limiting example, in one embodiment, $R_{24}$, $R_{26}$, and $R_{28}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s, and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid such as acetate and lactate, and any other anion that is compatible with the ammonium including an ester function, are other non-limiting examples of anions that may be used according to the present invention. In one embodiment, the anion $X^-$ is chosen from chloride and methyl sulfate.

In another embodiment, the ammonium salts of formula (B6) may be used, wherein:
$R_{22}$ is chosen from methyl and ethyl radicals,
x and y are equal to 1;
z is equal to 0 or 1;
r, s, and t are equal to 2;
$R_{23}$ is chosen from:
the radical below:

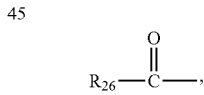

methyl, ethyl, and $C_{14}$-$C_{22}$ hydrocarbon-based radicals, hydrogen;
$R_{25}$ is chosen from:
the radical below:

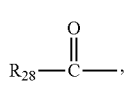

and hydrogen;
$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (B6) that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, and mixtures thereof. In one embodiment, the acyl radicals may include from 14 to 18 carbon atoms, and may be derived, for example, from a plant oil, for instance palm oil and sunflower oil. When the compound includes several acyl radicals, these radicals may be identical or different.

These products may be obtained, for example, by direct esterification of optionally oxyalkylenated triethanolamine, triisopropanolamine, alkyldiethanolamine, or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the composition according to the present invention include the ammonium salts including at least one ester function described in U.S. Pat. Nos. 4,874,554 and 4,137,180.

The quaternary ammonium salts mentioned above that may be used in the composition according to the present invention include, but are not limited to, those corresponding to formula (I), for example tetraalkylammonium chlorides, for instance dialkyldimethylammonium and alkyltrimethylammonium chlorides in which the alkyl radical includes from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate) ammonium chloride, sold under the name "Ceraphyl® 70" by the company Van Dyk.

According to one embodiment, the cationic surfactant that may be used in the composition according to the present invention is chosen from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(c-4) Nonionic Surfactants

The composition according to the present invention may comprise at least one nonionic surfactant. Two or more nonionic surfactants may be used in combination.

The nonionic surfactants are compounds well known in and of themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols, and esters of fatty acids, these compounds being ethoxylated, propoxylated, or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol $(C_6-C_{24})$alkylpolyglycosides; N—$(C_6-C_{24})$alkylglucamine derivatives; amine oxides such as $(C_{10}-C_{14})$alkylamine oxides or N—$(C_{10}-C_{14})$acylaminopropylmorpholine oxides; silicone surfactants; and mixtures thereof.

The nonionic surfactants may preferably be chosen from monooxyalkylenated, polyoxyalkylenated, monoglycerolated, or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:

monooxyalkylenated or polyoxyalkylenated $(C_8-C_{24})$alkylphenols, saturated or unsaturated, linear or branched, monooxyalkylenated or polyoxyalkylenated $C_8-C_{30}$ alcohols, saturated or unsaturated, linear or branched, monooxyalkylenated or polyoxyalkylenated $C_8-C_{30}$ amides, esters of saturated or unsaturated, linear or branched, $C_8-C_{30}$ acids and of polyalkylene glycols, monooxyalkylenated or polyoxyalkylenated esters of saturated or unsaturated, linear or branched, $C_8-C_{30}$ acids, and of sorbitol, saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated saturated fatty alcohol (or $C_8-C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 10 to 30 oxyethylene units (Steareth-10 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

Examples of polyoxyethylenated unsaturated fatty alcohol (or $C_8$-$C_{30}$ alcohols) that may be mentioned include the adducts of ethylene oxide with oleyl alcohol, especially those containing from 2 to 50 oxyethylene units and more particularly those containing from 10 to 40 oxyethylene units (Oleth-10 to Oleth-40, as the CTFA names); and mixtures thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

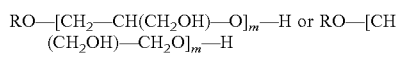

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl. Ether), oleyl alcohol containing 2 mol of glycerol (INCI name: Polyglyceryl-2 oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use a $C_8/C_{10}$ alcohol containing 1 mol of glycerol, a $C_{10}/C_{12}$ alcohol containing 1 mol of glycerol, and a $C_{12}$ alcohol containing 1.5 mol of glycerol.

The monoglycerolated or polyglycerolated $C_8$-$C_{40}$ fatty esters may correspond to the following formula:

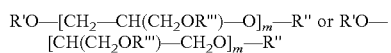

in which each of R', R", and R''' independently represents a hydrogen atom, or a linear or branched $C_8$-$C_{40}$ and preferably $C_8$-$C_{30}$ alkyl-CO— or alkenyl-CO-radical, with the proviso that at least one of R', R", and R''' is not a hydrogen atom, and m represents a number ranging from 1 to 30 and preferably from 1.5 to 10.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (CTFA names: PEG-9 laurate to PEG-50 laurate); PEG-9 to PEG-50 palmitate (CTFA names: PEG-9 palmitate to PEG-50 palmitate); PEG-9 to PEG-50 stearate (CTFA names: PEG-9 stearate to PEG-50 stearate); PEG-9 to PEG-50 palmitostearate; PEG-9 to PEG-50 behenate (CTFA names: PEG-9 behenate to PEG-50 behenate); polyethylene glycol 100 EO monostearate (CTFA name: PEG-100 stearate); and mixtures thereof.

According to one of the embodiments of the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids, and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids, and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids, and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di-, and/or tristearate) (CTFA name: glyceryl stearate), glyceryl laurate or glyceryl ricinoleate, and mixtures thereof can be cited, and as polyoxyalkylenated derivatives thereof, mono-, di-, or triester of fatty acids with a polyoxyalkylenated glycerol (mono-, di-, or triester of fatty acids with a polyalkylene glycol ether of glycerol), preferably polyoxyethylenated glyceryl stearate (mono-, di-, and/or tristearate), such as PEG-20 glyceryl stearate (mono-, di-, and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate, and esters of fatty acids, and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85), or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate, and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or a branched $C_{12}$-$C_{22}$ acyl chain such as an oleyl or isostearyl group. More preferably, the nonionic surfactant according to the present invention is PEG-20 glyceryl triisostearate.

According to one of the embodiments of the present invention, the nonionic surfactant may be selected from copolymers of ethylene oxide and of propylene oxide, in particular copolymers of the following formula:

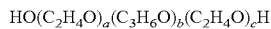

$$HO(C_2H_4O)_a(C_3H_6O)_b(C_2H_4O)_cH$$

in which a, b, and c are integers such that a+c ranges from 2 to 100 and b ranges from 14 to 60, and mixtures thereof.

According to one of the embodiments of the present invention, the nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

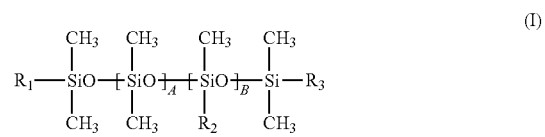

in which:
$R_1$, $R_2$, and $R_3$, independently of each other, represent a $C_1$-$C_6$ alkyl radical or a radical —$(CH_2)_x$—$(OCH_2CH_2)_y$—$(OCH_2CH_2)_z$—$OR_4$, at least one radical $R_1$, $R_2$, or $R_3$ not being an alkyl radical; $R_4$ being a hydrogen, an alkyl radical, or an acyl radical;
A is an integer ranging from 0 to 200;
B is an integer ranging from 0 to 50; with the proviso that A and B are not simultaneously equal to zero;
x is an integer ranging from 1 to 6;
y is an integer ranging from 1 to 30;
z is an integer ranging from 0 to 5.

According to one preferred embodiment of the present invention, in the compound of formula (I), the alkyl radical is a methyl radical, x is an integer ranging from 2 to 6, and y is an integer ranging from 4 to 30.

As examples of silicone surfactants of formula (I), mention may be made of the compounds of formula (II):

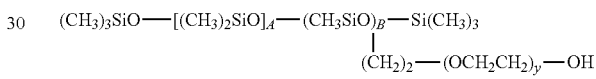

in which A is an integer ranging from 20 to 105, B is an integer ranging from 2 to 10, and y is an integer ranging from 10 to 20.

As examples of silicone surfactants of formula (I), mention may also be made of the compounds of formula (III):

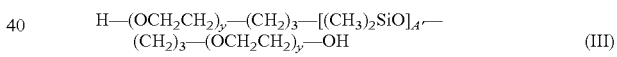

in which A' and y are integers ranging from 10 to 20.

Compounds of the present invention which may be used are those sold by the company Dow Corning under the names DC 5329, DC 7439-146, DC 2-5695, and Q4-3667. The compounds DC 5329, DC 7439-146, and DC 2-5695 are compounds of formula (II) in which, respectively, A is 22, B is 2, and y is 12; A is 103, B is 10, and y is 12; A is 27, B is 3, and y is 12.

The compound Q4-3667 is a compound of formula (III) in which A is 15 and y is 13.

[Water]

The composition according to the present invention includes (d) water.

The amount of the (d) water in the composition according to the present invention may range from 1% to 99% by weight, preferably from 10% to 90% by weight, more preferably from 20% to 80% by weight, even more preferably from 30 to 70% by weight, and further even more preferably from 40 to 60% by weight, relative to the total weight of the composition.

The (d) water can form an aqueous phase of the composition according to the present invention.

If the composition according to the present invention is in the form of an O/W emulsion, the (d) water in the composition according to the present invention can form a continuous aqueous phase in the O/W emulsion.

If the composition according to the present invention is in the form of a W/O emulsion, the (d) water in the composition according to the present invention can form dispersed aqueous phases in the W/O emulsion.

The amount of the aqueous phase in the composition according to the present invention may range from 1% to 99% by weight, preferably from 10% to 90% by weight, more preferably from 20% to 80% by weight, even more preferably from 30 to 70% by weight, and further even more preferably from 40 to 60% by weight, relative to the total weight of the composition.

[Additional Oil-Absorbable Particle]

The composition according to the present invention may include at least one (e) additional oil-absorbable particle. If two or more (e) additional oil-absorbable particles are used, they may be the same or different.

The (e) additional oil-absorbable particle is capable of absorbing (and/or adsorbing) an oil or a liquid fatty substance, for instance sebum (from the skin).

It is preferable that the (e) additional oil-absorbable particle have an oil-absorbing capacity of 140 ml/100 g or more, more preferably 250 ml/100 g or more, even more preferably 400 ml/100 g or more, further more preferably 600 ml/100 g or more, even further more preferably 800 ml/100 g or more, and further still more preferably 1000 ml/100 g or more.

The (e) additional oil-absorbable particle may have an oil-absorbing capacity of 2200 ml/100 g or less, preferably 2000 ml/100 g or less, more preferably 1800 ml/100 g or less, even more preferably 1600 ml/100 g or less, further more preferably 1400 ml/100 g or less, and even further more preferably 1200 ml/100 g or less.

Thus, the (e) additional oil-absorbable particle may have an oil-absorbing capacity ranging from 140 ml/100 g to 2200 ml/100 g, preferably from 250 ml/100 g to 2000 ml/100 g, even more preferably from 400 ml/100 g to 1800 ml/100 g, further more preferably from 600 ml/100 g to 1600 ml/100 g, even further more preferably from 800 ml/100 g to 1400 ml/100 g, and further still even more preferably from 1000 ml/100 g to 1200 ml/100 g.

The amount of oil absorbed (and/or adsorbed) by the (e) additional oil-absorbable particle may be characterized by measuring the wet point according to the method described below. The oil-absorbing capacity measured at the wet point, noted Wp, corresponds to the amount of oil that needs to be added to 100 g of particle in order to obtain a homogeneous paste.

The amount of the absorbed (and/or adsorbed) oil can be measured according to the method for determining the oil uptake of a powder described in standard ISO 787/5-1980. It corresponds to the amount of oil absorbed/adsorbed onto the available surface of the powder, by measuring the wet point.

An amount m (in grams) of the (e) additional oil-absorbable particle of between about 0.5 g and about 5 g (the amount depends on the density of the (e) additional oil-absorbable particle, but typically 2 g) is placed on a glass plate and isononyl isononanoate is then added dropwise.

After addition of 4 to 5 drops of purified linseed oil, the isononyl isononanoate is incorporated into the (a) oil-absorbable organic particle using a spatula, and addition of the isononyl isononanoate is continued until a conglomerate of isononyl isononanoate and powder has formed. At this point, the isononyl isononanoate is added one drop at a time and the mixture is then triturated with the spatula. The addition of isononyl isononanoate is stopped when a firm, smooth paste is obtained. This paste must be able to be spread on the glass plate without cracking or forming lumps. The volume Vs (expressed in ml) of isononyl isononanoate used is then noted.

The oil uptake corresponds to the ratio Vs/m.

In the above protocol to determine the wet point, isononyl isononanoate may be replaced with oleic acid or linseed oil. Unless otherwise defined, oil-absorbing capacities defined in the present invention mean those measured by using isononyl isononanoate.

The (e) additional oil-absorbable particle may have a volume-average particle size of less than 50 µm, preferably less than 45 µm, and more preferably less than 40 µm. Unless otherwise defined, particle sizes or average particle sizes defined in the present invention mean volume-average particle sizes.

The (e) additional oil-absorbable particle may have a volume-average particle size of 1 µm or more, preferably 2 µm or more, more preferably 3 µm or more, and even more preferably 4 µm or more.

The (primary) particle size of the (e) additional oil-absorbable particle may be from 1 to 30 µm, preferably from 2 to less than 25 µm, more preferably from 3 to less than 20 µm, and even more preferably from 4 to less than 15 µm. The (primary) particle size can be measured by, for example, extracting and measuring from a photograph image obtained by SEM and the like, using a particle size analyzer such as a laser diffraction particle size analyzer, and the like. It is preferable to use a particle size analyzer such as a laser diffraction particle size analyzer. In this case, the (primary) particle size is the volume-average (primary) particle size.

It is preferable that the (e) additional oil-absorbable particle be a porous particle, in particular a porous spherical particle.

According to another aspect of the present disclosure, the (e) additional oil-absorbable particle may have a BET specific surface area greater than or equal to 300 m$^2$/g, for instance, greater than or equal to 500 m$^2$/g, such as greater than or equal to 600 m$^2$/g, and less than or equal to 1500 m$^2$/g.

The (e) additional oil-absorbable particle may have a density of from 0.01 to 0.9 g/cm$^3$, preferably from 0.05 to 0.5 g/cm$^3$, and more preferably from 0.1 to 0.3 g/cm$^3$.

It is preferable that the oil-absorbing capacity of the total of the (a) oil-absorbable organic particle and the (e) additional oil-absorbable particle in the composition according to the present invention be more than 170 ml/100 g, preferably more than 200 ml/100 g, and more preferably more than 250 ml/100 g.

It is also preferable that the oil-absorbing capacity of the total of the powder ingredients in the composition according to the present invention be more than 170 ml/100 g, preferably more than 200 ml/100 g, and more preferably more than 250 ml/100 g.

The (e) additional oil-absorbable particle(s) may be present in the composition according to the present invention in an amount ranging from 0.01 to 20% by weight, preferably ranging from 0.05 to 15% by weight, more preferably ranging from 0.1 to 10% by weight, and even more preferably ranging from 0.1 to 5% by weight, relative to the total weight of the composition.

(Inorganic Additional Oil-Absorbable Particle)

The (e) additional oil-absorbable particle may be of inorganic nature.

The inorganic (e) additional oil-absorbable particle may have at least one inorganic core and at least one hydrophobic coating.

The hydrophobic coating may be formed by a hydrophobic treatment agent which may be chosen especially from fatty acids such as stearic acid; metal soaps such as aluminium dimyristate, the aluminium salt of hydrogenated tallow glutamate; amino acids; N-acylamino acids or salts thereof; lecithin, isopropyl triisostearyl titanate, mineral waxes, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl, or cocoyl group. The salts of these compounds may be aluminium, magnesium, calcium, zirconium, zinc, sodium, or potassium salts. The amino acid may be, for example, lysine, glutamic acid, or alanine.

The term "alkyl" mentioned in the compounds mentioned previously especially denotes an alkyl group containing from 1 to 30 carbon atoms and preferably containing from 5 to 16 carbon atoms.

It is preferable that the inorganic (e) additional oil-absorbable particle comprise at least one material selected from the group consisting of silica, in particular hydrophobic silica such as silica silylate, silicate, perlite, boron nitride, magnesium carbonate, magnesium hydroxide, kaolin, talc, and a mixture thereof.

The hydrophobic silica, in particular silica silylate, may be based on silica aerogels which are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J. and Scherer G. W., Sol-Gel Science, New York, Academic Press, 1990.

The hydrophobic silica aerogel particles may exhibit a specific surface area per unit of weight (SW) ranging from 500 to 1500 $m^2/g$, preferably from 600 to 1200 $m^2/g$, and more preferably from 600 to 800 $m^2/g$, and/or a size, expressed as the volume-average diameter (D[0.5]), ranging from 1 to 1500 µm, preferably from 1 to 1000 µm, more preferably from 1 to 100 µm, in particular from 1 to 30 µm, even more preferably from 5 to 25 further more preferably from 5 to 20 µm, and even further more preferably from 5 to 15 µm.

According to one embodiment, the hydrophobic silica aerogel particles may exhibit a size, expressed as volume-average diameter (D[0.5]), ranging from 1 to 30 µm, preferably from 5 to 25 more preferably from 5 to 20 µrn, and even more preferably from 5 to 15 µm.

The specific surface area per unit of weight can be determined by the nitrogen absorption method, known as the BET (Brunauer-Emmett-Teller) method, described in The Journal of the American Chemical Society, Vol. 60, page 309, February 1938, which corresponds to international standard ISO 5794/1 (appendix D). The BET specific surface area corresponds to the total specific surface area of the particles under consideration.

The sizes of the silica aerogel particles can be measured by static light scattering using a commercial particle size analyzer of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

According to an advantageous embodiment, the hydrophobic silica aerogel particles may exhibit a specific surface area per unit of weight (SW) ranging from 600 to 800 $m^2/g$ and a size, expressed as the volume-average diameter (D[0.5]), ranging from 5 to 20 µm, and preferably from 5 to 15 µm.

The silica aerogel particles can advantageously exhibit a packed density ($\tau$) ranging from 0.04 $g/cm^3$ to 0.10 $g/cm^3$, and preferably from 0.05 $g/cm^3$ to 0.08 $g/cm^3$.

In the context of the present invention, this density, known as the packed density, can be assessed according to the following protocol:

40 g of powder are poured into a graduated measuring cylinder;

the measuring cylinder is then placed on a Stay 2003 device from Stampf Volumeter;

the measuring cylinder is subsequently subjected to a series of 2500 packing actions (this operation is repeated until the difference in volume between 2 consecutive tests is less than 2%); and the final volume Vf of packed powder is then measured directly on the measuring cylinder. The packed density is determined by the ratio w/Vf, in this instance 40/Vf (Vf being expressed in $cm^3$ and w in g).

According to one embodiment, the hydrophobic silica aerogel particles may exhibit a specific surface area per unit of volume SV ranging from 5 to 60 $m^2/cm^3$, preferably from 10 to 50 $m^2/cm^3$, and more preferably from 15 to 40 $m^2/cm^3$.

The specific surface area per unit of volume is given by the relationship: $S_v = S_w \times \rho$; where $\rho$ is the packed density expressed in $g/cm^3$ and $S_w$ is the specific surface area per unit of weight expressed in $m^2/g$, as defined above.

The term "hydrophobic silica" is understood to mean any silica, the surface of which is treated with silylating agents, for example with halogenated silanes, such as alkylchlorosilanes, siloxanes, in particular dimethylsiloxanes, such as hexamethyldisiloxane, or silazanes, so as to functionalize the OH groups with silyl groups Si—Rn, for example, trimethylsilyl groups.

As regards the preparation of hydrophobic silica aerogel particles modified at the surface by silylation, reference may be made to the document U.S. Pat. No. 7,470,725.

Use will in particular be made of hydrophobic silica aerogel particles modified at the surface with trimethylsilyl groups.

Examples of inorganic (e) additional oil-absorbable particle include the fillers described below:

Silica powders that may be mentioned include polydimethylsiloxane-coated amorphous silica microspheres, especially those sold under the name of SA Sunsphere® H33 (oil uptake equal to 243 ml/100 g), precipitated silica powders surface-treated with a mineral wax, such as precipitated silica treated with a polyethylene wax, and especially those sold under the name Acematt OR 412 by the company Evonik-Degussa (oil uptake equal to 398 ml/100 g), Sunsphere® 12 (isononyl isononanoate oil uptake equal to 140.6 ml/100 g) by the company AGC Si-Tech, and silica silylate sold under the name of VM-2270 (isononyl isononanoate oil uptake equal to 1090 ml/100 g) by the company Dow Corning.

Silica powders that may be mentioned include
porous silica microspheres, especially those sold under the
names Sunsphere® H53 and Sunsphere® 1133 (oil uptake
equal to 370 ml/100 g) by the company Asahi Glass;
MSS-500-3H by the company Kobo; amorphous hollow
silica particles, especially those sold under the name Silica
Shells by the company Kobo (oil uptake equal to 550 ml/100
g);
porous silica microsphere sold under the name of Sylysia
350 (oil uptake equal to 310 ml/100 g) by the company Fuji
Silysia Chemical; and
silica powder sold under the name of Finesil X35 (oil uptake
equal to 380 ml/100 g) by the company Oriental Silicas.

Perlite powders that may be mentioned include perlite
sold under the name of
Optimat® 1430 OR and Optimat® 2550 OR (isononyl
isononanoate oil uptake equal to 250 ml/100 g) by the
company World Minerals, and
Perlite-MSZ12 (isononyl isononanoate oil uptake equal to
148.2 ml/100 g) by the company Miyoshi Kasei.

A silicate that may especially be mentioned is aluminum
silicate which is sold under the name of Kyowaad® 700PEL
(oil uptake equal to 195 ml/100 g) by the company Kyowa
Chemical Industry.

A magnesium carbonate powder that may especially be
mentioned is the product sold under the name Tipo Carbomagel® by the company Buschle & Lepper (oil uptake
equal to 214 ml/100 g).

A magnesium carbonate/magnesium hydroxide powder
that may especially be mentioned is the product of
$mMgCO_3$—$Mg(OH)_2$-$nH_2O$ which is sold under the name
of Mg Tube (oil uptake equal to 250-310 ml/100 g) by the
company Nittesu Mining.

It is more preferable to use, as the inorganic (e) additional
oil-absorbable particle, silica silylate sold under the name
VM-2270 by Dow Corning, the particles of which exhibit an
average size ranging from 5 to 15 microns and a specific
surface area per unit of weight ranging from 600 to 800
$m^2/g$.

The inorganic (e) additional oil-absorbable particle(s)
may be present in the composition according to the present
invention in an amount ranging from 0.01 to 20% by weight,
preferably ranging from 0.05 to 15% by weight, more
preferably ranging from 0.1 to 10% by weight, and even
more preferably ranging from 0.1 to 5% by weight, relative
to the total weight of the composition.
(Organic Oil-Absorbable Particle)

The (e) additional oil-absorbable particle may be of
organic nature.

The organic (e) additional oil-absorbable particle may
comprise at least one material chosen from the group
consisting of polyamide (in particular Nylon-6) powders,
powders of acrylic polymers, especially of polymethyl
methacrylate, of polymethyl methacrylate/ethylene glycol
dimethacrylate, of polyallyl methacrylate/ethylene glycol
dimethacrylate or of ethylene glycol dimethacrylate/lauryl
methacrylate copolymer; silicones; and a mixture thereof.
The above material may be crosslinked.

It may be preferable that the organic (e) additional oil-absorbable particle be selected from powders of acrylic
polymers, especially of ethylene glycol dimethacrylate/lauryl methacrylate copolymer, acrylate copolymer, methyl
methacrylate crosspolymer, and silicone resins.

The organic (e) additional oil-absorbable particle may,
where appropriate, be surface-treated with at least one
hydrophobic treatment agent.

This hydrophobic treatment agent may be chosen, for
example, from:
 silicones, such as methicones and dimethicones;
 fatty acids, such as stearic acid;
 metallic soaps, such as aluminium dimyristate and aluminium salt of hydrogenated tallow glutamate;
 perfluoroalkyl phosphates, perfluoroalkyl silanes, perfluoroalkyl silazanes, hexafluoropropylene polyoxides, and polyorganosiloxanes comprising perfluoroalkyl perfluoropolyether groups;
 amino acids, N-acylated amino acids, and their salts;
 lecithin, and isopropyl triisostearyl titanate; and
 mixtures thereof.

As used herein, the term "alkyl" mentioned in the compounds cited above is understood to mean a linear, branched
or cyclic alkyl group comprising from 1 to 30, atoms, for
example, from 5 to 16 carbon atoms.

The N-acylated amino acids may comprise an acyl group
comprising from 8 to 22 carbon atoms, such as, for example,
a 2-ethylhexanoyl, caproyl, lauroyl, myristoyl, palmitoyl,
stearoyl, and cocoyl group. The salts of these components
may be the aluminium, magnesium, calcium, zirconium,
zinc, sodium, or potassium salts. The amino acid may be, for
example, lysine, glutamic acid, or alanine.

Examples of the organic (e) additional oil-absorbable
particle include the fillers described below:
 Acrylic polymer powders that may be mentioned include
porous polymethyl methacrylate/ethylene glycol dimethacrylate spheres sold under the name Microsponge 5640 by
the company Cardinal Health Technologies (oil uptake equal
to 155 ml/100 g),
vinyl dimethicone/methicone silsesquioxane crosspolymer
sold under the name of KSP 100 (isononyl isononanoate oil
uptake equal to 142.7 ml/100 g) by the company Shin Etsu.
ethylene glycol dimethacrylate/lauryl methacrylate crosslinked copolymer powders, especially those sold under the
name Polytrap® 6603 from the company Amcol Health &
Beauty Solutions (isononyl isononanoate oil uptake equal to
657 ml/100 g), and acrylonitrile/methyl methacrylate/vinylidene chloride copolymer sold under the name Expancel
551DE40D42 (isononyl isononanoate oil uptake equal to
1387 ml/100 g) by the company Akzo Novel.

Polyamide powders that may be mentioned include
nylon-6 powder, especially the product sold under the name
Pomp610 by the company UBE Industries (oil uptake equal
to 202 ml/100 g).

The organic (e) additional oil-absorbable particle(s) may
be present in the composition according to the present
invention in an amount ranging from 0.01 to 20% by weight,
preferably ranging from 0.05 to 15% by weight, more
preferably ranging from 0.1 to 10% by weight, and even
more preferably ranging from 0.1 to 5% by weight, relative
to the total weight of the composition.
[Other Ingredients]

The composition according to the present invention may
also include at least one optional or additional ingredient.

The amount of the optional or additional ingredient(s) is
not limited, but may be from 0.01% to 30% by weight,
preferably from 0.1% to 20% by weight, and more preferably from 1% to 10% by weight, relative to the total weight
of the composition according to the present invention.

The optional or additional ingredient(s) may be selected
from the group consisting of anionic, cationic, nonionic, or
amphoteric polymers; thickeners; organic or inorganic UV
filters; peptides and derivatives thereof; protein hydrolyzates; swelling agents and penetrating agents; agents for
combating hair loss; anti-dandruff agents; natural or synthetic thickeners for oils; suspending agents; sequestering agents; opacifying agents; dyes; sunscreen agents; vitamins or provitamins; fragrances; preservatives, co-preservatives, stabilizers; and mixtures thereof.

The composition according to the present invention may include one or several cosmetically acceptable organic solvents, which may be alcohols: in particular monovalent alcohols such as ethyl alcohol, isopropyl alcohol, benzyl alcohol, and phenylethyl alcohol; diols such as ethylene glycol, propylene glycol, and butylene glycol; other polyols such as glycerol, sugar, and sugar alcohols; and ethers such as ethylene glycol monomethyl, monoethyl, and monobutyl ethers, propylene glycol monomethyl, monoethyl, and monobutyl ether, and butylene glycol monomethyl, monoethyl, and monobutyl ethers.

The organic solvent(s) may then be present in a concentration of from 0.01% to 30% by weight, preferably from 0.1% to 20% by weight, and more preferably from 1% to 15% by weight, relative to the total weight of the composition.

The composition according to the present invention may further comprise at least one selected from the group consisting of polyols, thickeners, preservatives, co-preservatives, and mixtures thereof.

[Form]

The composition according to the present invention is in the form of an emulsion such as a W/O emulsion, an O/W emulsion, or the like.

[Cosmetic Process]

The composition according to the present invention may preferably be used as a cosmetic composition. The cosmetic composition may be a skin cosmetic composition, such as a skin care composition and a skin make up composition. The skin here encompasses face skin, neck skin, and the scalp. The composition according to the present invention may also be used for mucosae such as the lips, and the like.

In particular, the composition according to the present invention may be intended for application onto a keratin substance such as the skin or lips, preferably the skin. Thus, the composition according to the present invention can be used for a cosmetic process for the skin.

The cosmetic process or cosmetic use for a keratin substance such as the skin, according to the present invention comprises, at least, the step of applying onto the keratin substance the composition according to the present invention.

The cosmetic process or cosmetic use according to the present invention can provide anti-sebum effects or anti-shine effects due to the association of at least the ingredients (a) to (d) in the composition according to the present invention.

The present invention has an aspect of a use of
(a) at least one oil-absorbable organic particle which has an oil-absorbing capacity of 170 ml/100 g or more, preferably 250 ml/100 g or more, and more preferably 400 ml/100 g or more, and a volume-average particle size of less than 30 μm, preferably less than 25 μm, and more preferably less than 20 μm,
in an emulsion comprising (b) at least one oil, (c) at least one emulsifier, and (d) water, in order to provide the emulsion with long-lasting matte effects and excellent texture resulting, for example, in smooth application.

EXAMPLES

The present invention will be described in a more detailed manner by way of examples. However, these examples should not be construed as limiting the scope of the present invention. The examples below are presented as non-limiting illustrations in the field of the present invention.

Examples 1-6 and Comparative Examples 1-9

The following compositions according to Examples 1-6 and Comparative Examples 1-9, shown in Tables 1-3, were prepared by mixing the ingredients shown in Tables 1-3 at room temperature. The numerical values for the amounts of the ingredients shown in Tables 1-3 are all based on "% by weight" as active raw materials.

TABLE 1

| (W/O emulsion) | | | | | |
|---|---|---|---|---|---|
| | Ex. 1 | Ex. 2 | Comp. Ex. 1 | Comp. Ex. 2 | Comp. Ex. 3 |
| Porous Polylactic Acid Particle (Toraypearl ® PLA, Toray Industries Inc.) | 3.00 | 5.00 | — | — | — |
| Non-Porous Polylactic Acid Particle (Ecosoft 608XF, Micro Powders) | — | — | 3.00 | 5.00 | — |
| Dimethicone | 16.00 | 16.00 | 16.00 | 16.00 | 16.00 |
| Dimethicone - PEG/PPG-18/8 Dimethicone | 2.00 | 2.00 | 2.00 | 2.00 | 2.00 |
| PEG-10 Dimethicone | 2.00 | 2.00 | 2.00 | 2.00 | 2.00 |
| Dimethicone - Dimethicone Crosspolymer | 10.00 | 10.00 | 10.00 | 10.00 | 10.00 |
| Ethylhexyl Methoxycinnamate | 6.00 | 6.00 | 6.00 | 6.00 | 6.00 |
| Tribehenin | 1.00 | 1.00 | 1.00 | 1.00 | 1.00 |
| Water | qsp 100 | qsp 100 | qsp 100 | qsp 100 | qsp 100 |
| Glycerin | 3.00 | 3.00 | 3.00 | 3.00 | 3.00 |
| Butylene Glycol | 2.00 | 2.00 | 2.00 | 2.00 | 2.00 |
| Caprylyl Glycol | 0.50 | 0.50 | 0.50 | 0.50 | 0.50 |
| Phenoxyethanol | 0.50 | 0.50 | 0.50 | 0.50 | 0.50 |
| Magnesium Sulfate | 0.70 | 0.70 | 0.70 | 0.70 | 0.70 |
| Ethyl Alcohol | 4.00 | 4.00 | 4.00 | 4.00 | 4.00 |
| Haze | 82.7 | 90.3 | 54.1 | 64.8 | 54.6 |
| Matteness | 84.4 | 71.4 | 37.2 | 50.5 | 24.7 |
| Wear of Matteness | 9.4 | 3.4 | 40.4 | 32.2 | 13.4 |

TABLE 2

| (O/W emulsion) | | | | | |
|---|---|---|---|---|---|
| | Ex. 3 | Ex. 4 | Comp. Ex. 4 | Comp. Ex. 5 | Comp. Ex. 6 |
| Porous Polylactic Acid Particle (Toraypearl ® PLA, Toray Industries Inc.) | 3.00 | 5.00 | — | — | — |
| Non-Porous Polylactic Acid Particle (Ecosoft 608XF, Micro Powders) | — | — | 3.00 | 5.00 | — |
| Water | qsp 100 | qsp 100 | qsp 100 | qsp 100 | qsp 100 |
| Caprylyl Glycol | 0.50 | 0.50 | 0.50 | 0.50 | 0.50 |
| Phenoxyethanol | 0.50 | 0.50 | 0.50 | 0.50 | 0.50 |
| Carbomer | 0.30 | 0.30 | 0.30 | 0.30 | 0.30 |
| Triethanolamine | 0.30 | 0.30 | 0.30 | 0.30 | 0.30 |
| Glyceryl Stearate - PEG-100 Stearate | 2.50 | 2.50 | 2.50 | 2.50 | 2.50 |
| PEG-40 Stearate | 2.50 | 2.50 | 2.50 | 2.50 | 2.50 |
| Cetyl Alcohol | 1.00 | 1.00 | 1.00 | 1.00 | 1.00 |
| Stearyl Alcohol | 1.00 | 1.00 | 1.00 | 1.00 | 1.00 |
| Hydrogenated Polyisobutene | 5.00 | 5.00 | 5.00 | 5.00 | 5.00 |
| Isohexadecane | 15.00 | 15.00 | 15.00 | 15.00 | 15.00 |
| Haze | 71.8 | 84.3 | 44.4 | 55.1 | 6.0 |

TABLE 3

(O/W emulsion)

|  | Ex. 5 | Ex. 6 | Comp. Ex. 7 | Comp. Ex. 8 | Comp. Ex. 9 |
|---|---|---|---|---|---|
| Porous Polylactic Acid Particle (Toraypearl ® PLA, Toray Industries Inc.) | 3.00 | 5.00 | — | — | — |
| Non-Porous Polylactic Acid particle (Ecosoft 608XF, Micro Powders) | — | — | 3.00 | 5.00 | — |
| Water | qsp 100 | qsp 100 | qsp 100 | qsp 100 | qsp 100 |
| Glycerin | 7.00 | 7.00 | 7.00 | 7.00 | 7.00 |
| Propylene Glycol | 2.00 | 2.00 | 2.00 | 2.00 | 2.00 |
| Ammonium Polyacryloyldimethyl Taurate | 1.00 | 1.00 | 1.00 | 1.00 | 1.00 |
| Saccharide Gum | 2.00 | 2.00 | 2.00 | 2.00 | 2.00 |
| Ethanol | 8.00 | 8.00 | 8.00 | 8.00 | 8.00 |
| Dimethicone | 7.00 | 7.00 | 7.00 | 7.00 | 7.00 |
| PEG-12 Dimethicone | 0.70 | 0.70 | 0.70 | 0.70 | 0.70 |
| Dimethicone (5cst) | 4.00 | 4.00 | 4.00 | 4.00 | 4.00 |
| In-vitro Anti-Shine Index | Good | Good | Poor | Poor | 0 |

The properties of the porous polylactic acid particle and the non-porous polylactic acid particle are as shown in Table 4.

TABLE 4

|  |  | Porous Polylactic Acid Particle | Non-Porous Polylactic Acid Particle |
|---|---|---|---|
| Average Particle Size (μm) |  | 11.0 | 8.0 |
| Powder Density (g/cm³) |  | 0.12 | 1.24 |
| Absorption capacity (ml/100 g) | Isononyl Isononanoate | 465.9 | 77.6 |
|  | Oleic Acid | 456.2 | 97.8 |
|  | Dimethicone | 478.2 | 78.2 |
|  | Water | 384 | 61 |

[Evaluations]

The compositions according to Examples 1-6 and Comparative Examples 1-9 were evaluated as follows.

(Haze)

The haze value of each of the compositions according to Examples 1-4 and Comparative Examples 1-6 in the form of a layer of 25 μm were measured with a Hazeguard (BYK).

The results are shown in Tables 1 and 2.

The results shown in Tables 1 and 2 show that the compositions according to the present invention (Examples 1-4) have higher haze values than the compositions according to Comparative Examples 1-6, which means that the present invention can diffuse more light, and therefore, the present invention can exert higher matte effects.

(Matteness)

Each of the compositions according to Examples 1 and 2, and Comparative Examples 1-3 was applied on a contrast card as a layer with a thickness of 50 and was dried for 24 hours at room temperature.

The reflectance on the above layer after the application of the composition thereon was measured with a goniophotometer (GP-5, Murakami) as a 45° gloss value. The amount of the composition was the same as each other. A lower 45° gloss value shows better results.

The results are shown in Table 1.

The results shown in Table 1 show that the compositions according to the present invention (Examples 1 and 2) can provide better matteness than the compositions according to Comparative Examples 1-3, which means that the present invention can exert higher immediate matte effects.

(Wear of Matteness)

Each of the compositions according to Examples 1 and 2, and Comparative Examples 1-3 was applied on a contrast card as a layer with a thickness of 25 μm, and was maintained for 20 minutes at 35° C.

The reflectance on the above layer was measured with a glossmeter (GM-268, Konika Minolta) as a 60° gloss value (original).

3.0 g of each of the compositions according to Examples 1 and 2, and Comparative Examples 1-3 was mixed with 0.4 g of an artificial sebum/sweat composition, and the mixture thus obtained was applied on a contrast card as a layer with a thickness of 25 μm, and was maintained for 20 minutes at 35° C. The formulation of the artificial sebum/sweat composition is shown in Table 5 below.

TABLE 5

|  | (wt %) |
|---|---|
| Oleic acid | 20.0 |
| Poly(oxy-1,2-ethanediyl) | 1.0 |
| Water | 79.0 |
| Total | 100.0 |

The reflectance on the above layer was measured with a glossmeter (GM-268, Konika Minolta) as a 60° gloss value (mix).

The wear of matteness was calculated by the following equation:

Wear of Matteness=the 60° gloss value(mix)−the 60° gloss value(original)

A lower value of "wear of matteness" means better results. The results are shown in Table 1.

The results shown in Table 1 show that the compositions according to the present invention (Examples 1 and 2) have a lower value of "wear of matteness" than the compositions according to Comparative Examples 1-3, which means that the matte effects by the present invention are more resistant to sebum and/or sweat.

(In-Vitro Anti-Shine Index)

Each of the compositions according to Examples 5 and 6, and Comparative Examples 7-9 was applied on a contrast card as a layer with a thickness of 100 μm, and was dried for 24 hours at room temperature.

An artificial sebum/sweat composition with the formulation shown in the above Table 5 was sprayed on the above layer on the contrast card, at room temperature.

The reflectance on the above layer 9 minutes after the spraying of the artificial sebum/sweat composition thereon was measured with a glossmeter (GM-268, Konika Minolta) as a 60° gloss value. The amount of the artificial sebum/sweat composition sprayed on each of the above layers was the same as each other.

The anti-shine index was calculated by the following equation:

Anti-Shine Index=(Reflectance of a sample 9 minutes after the spraying)−(Reflectance of a negative control)/(Reflectance of a positive control 9 minutes after the spraying)−(Reflectance of a negative control)

As the negative control, the composition according to Comparative Example 9 was used. As the positive control, the composition according to Comparative Example 9 with the addition of silica silylate (aerogel) in an amount of 2% by weight relative to the total weight of the composition (the amount of water was reduced by 2% by weight) was used.

The determined anti-shine index was categorized as follows.
Good (long-lasting anti-shine effect): more than 70
Poor (short-lasting anti-shine effect): 70 or less The results are shown in Table 3.

The results shown in Table 3 show that the compositions according to the present invention (Examples 5 and 6) have better anti-shine index than the compositions according to Comparative Examples 7-9, which means that the matte effects by the present invention are more resistant to sebum and/or sweat.

Example 7 and Comparative Example 10

The following compositions according to Example 7 and Comparative Example 10, shown in Table 6, were prepared by mixing the ingredients shown in Table 6 at room temperature. The numerical values for the amounts of the ingredients shown in Table 6 are all based on "% by weight" as active raw materials.

TABLE 6

(O/W emulsion)

| | Ex. 7 | Comp. Ex. 10 |
|---|---|---|
| Porous Polylactic Acid Particle (Toraypearl ® PLA, Toray Industries Inc.) (465.9 ml/100 g)* (11 μm)** | 2.00 | — |
| Water | qsp 100 | qsp 100 |
| Glycerin | 7.00 | 7.00 |
| Propylene Glycol | 2.00 | 2.00 |
| Ammonium Polyacryloyldimethyl Taurate | 1.00 | 1.00 |
| Saccharide Gum | 2.00 | 2.00 |
| Ethanol | 8.00 | 8.00 |
| Dimethicone | 7.00 | 7.00 |
| PEG-12 Dimethicone | 0.70 | 0.70 |
| Dimethicone (5cst) | 4.00 | 4.00 |
| In-vivo Anti Shine Index | | |
| $T_0$ | 28.1 ± 5.9 | 28.2 ± 5.4 |
| $T_{10min} - T_0$ | −10.4 ± 2.8 | 0 |
| $T_{2h}$ | 30.9 ± 6.3 | 44.4 ± 5.4 |
| $T_{2h} - T_0$ | 2.8 ± 2.9 | 15.8 ± 5.6 |
| Sensory Tests | | |
| Application Smoothness | 11.8 | 10.0 |
| Skin Shine After 2 Minutes | 2 | 7 |

*oil* absorption capability based on isononyl isononanoate
**average particle size

[Evaluations]

The compositions according to Example 7 and Comparative Example 10 were evaluated as follows.

(In-Vivo Anti-Shine Index)

Each of the compositions according to Example 7, and Comparative Example 10 was applied on the face of 28 panelists, in a room with conditions of a temperature of 37° C. and a relative humidity of 80%, as a layer with a thickness of 100 μm.

The reflectance on the above layer just after the application of each composition thereon, 10 minutes after the application, and 2 hours after the application was measured with a glossmeter (GM-268, Konika Minolta) as a 60° gloss value.

The results are shown in Table 6. In Table 6, $T_0$ means the reflectance just after the application.

$T_{10min}$-$T_0$ means the difference between the reflectance 10 minutes after the application and $T_0$.

$T_{2h}$ means the reflectance 2 hours after the application.

$T_{2h}$-$T_0$ means the difference between the reflectance 2 hours after the application and $T_0$.

The results shown in Table 6 show that the composition according to the present invention (Example 7) has longer-lasting matte effects than Comparative Example 10, which means that the matte effects by the present invention can last for a longer period of time.

(Sensory Tests)

25 panelists evaluated "application smoothness" and "skin shine after 2 minutes" after the use of the same amount of each of the compositions according to Example 7 and Comparative Examples 10.

Each panelist took each composition in their hands, then applied it on their faces to evaluate "application smoothness" and "skin shine after 2 minutes" after the use of each composition, and rated it from 0 (low) to 15 (high).

The average scores are shown in Table 6.

The results shown in Table 6 show that the composition according to the present invention (Example 7) is better than the composition according to Comparative Example 10 in terms of smooth feeling of use and matte effects.

Examples 8-11 and Comparative Examples 11-13

The following compositions according to Examples 8-11 and Comparative Examples 11-13, shown in Table 7, were prepared by mixing the ingredients shown in Table 7 at room temperature. The numerical values for the amounts of the ingredients shown in Table 7 are all based on "% by weight" as active raw materials.

TABLE 7

(O/W emulsion)

| | Oil* Absorption Capability | Ex. 8 | Ex. 9 | Ex. 10 | Ex. 11 | Comp. Ex. 11 | Comp. Ex. 12 | Comp. Ex. 13 |
|---|---|---|---|---|---|---|---|---|
| Porous Polylactic Acid Particle (Toraypearl ® PLA, Toray Industries Inc.) (11 μm)** | 465.9 ml/100 g | 2.00 | 1.50 | 1.00 | 0.50 | — | — | — |
| Silica Silylate (Aerogel VM-2270, Dow Corning) | 1090 ml/100 g | — | 0.50 | 1.00 | 1.50 | — | 2.00 | — |
| Perlite | 132 ml/100 g | — | — | — | — | — | — | 2.00 |
| Water | — | qsp 100 | qsp 100 | qsp 100 | qsp 100 | qsp 100 | qsp 100 | qsp 100 |
| Glycerin | | 7.00 | 7.00 | 7.00 | 7.00 | 7.00 | 7.00 | 7.00 |
| Propylene Glycol | | 2.00 | 2.00 | 2.00 | 2.00 | 2.00 | 2.00 | 2.00 |

TABLE 7-continued (O/W emulsion)

| | Oil* Absorption Capability | Ex. 8 | Ex. 9 | Ex. 10 | Ex. 11 | Comp. Ex. 11 | Comp. Ex. 12 | Comp. Ex. 13 |
|---|---|---|---|---|---|---|---|---|
| Ammonium Polyacryloyldimethyl Taurate | — | 1.00 | 1.00 | 1.00 | 1.00 | 1.00 | 1.00 | 1.00 |
| Saccharide Gum | — | 2.00 | 2.00 | 2.00 | 2.00 | 2.00 | 2.00 | 2.00 |
| Ethanol | — | 8.00 | 8.00 | 8.00 | 8.00 | 8.00 | 8.00 | 8.00 |
| Dimethicone | — | 7.00 | 7.00 | 7.00 | 7.00 | 7.00 | 7.00 | 7.00 |
| PEG-12 Dimethicone | — | 0.70 | 0.70 | 0.70 | 0.70 | 0.70 | 0.70 | 0.70 |
| Dimethicone (5 cst) | — | 4.00 | 4.00 | 4.00 | 4.00 | 4.00 | 4.00 | 4.00 |
| Average Oil* Absorption Capacity of Powder Ingredients (ml/100 g) | | 460 | 560 | 730 | 865 | 0 | 1090 | 132 |
| In-vitro Anti-Shine Index | | Good | Good | Good | Good | 0 | Good | Poor |
| | | | Sensory Test | | | | | |
| Application Smoothness | | Very Good | Very Good | Very Good | Good | Good | Poor | Poor |

*isononyl isononanoate
**average particle size

[Evaluations]

The compositions according to Examples 8-11 and Comparative Examples 11-13 were evaluated as follows.

(In-Vitro Anti-Shine Index)

Each of the compositions according to Examples 8-11, and Comparative Examples 11-13 was applied on a contrast card as a layer with a thickness of 100 μm, and was dried for 24 hours at room temperature.

An artificial sebum/sweat composition with the formulation shown in the above Table 5 was sprayed on the above layer on the contrast card, at room temperature.

The reflectance on the above layer 9 minutes after the spraying of the artificial sebum/sweat composition thereon was measured with a glossmeter (GM-268, Konika Minolta) as a 60° gloss value. The amount of the artificial sebum/sweat composition sprayed on each of the above layers was the same as each other.

The anti-shine index was calculated by the following equation:

Anti-Shine Index=(Reflectance of a sample 9 minutes later)−(Reflectance of a negative control)/(Reflectance of a positive control 9 minutes later)−(Reflectance of a negative control)

As the negative control, the composition according to Comparative Example 11 was used. As the positive control, the composition according to Comparative Example 12 including silica silylate (aerogel) in an amount of 2% by weight relative to the total weight of the composition (the amount of water was reduced by 2% by weight) was used.

The determined anti-shine index was categorized as follows.

Good (long-lasting anti-shine effect): more than 70
Poor (short-lasting anti-shine effect): 70 or less The results are shown in Table 7.

The results shown in Table 7 also show that the compositions according to the present invention (Examples 8-11) can provide better matte effects which can last for a longer time than Comparative Examples 11 and 13, which means that the matte effects by the present invention are better and can last for a longer period of time.

(Sensory Tests)

25 panelists evaluated "application smoothness" after the use of the same amount of each of the compositions according to Examples 8-11 and Comparative Examples 11-13.

Each panelist took each composition in their hands, then applied it on their faces to evaluate "application smoothness" after the use of each composition, and rated it from 0 (low) to 15 (high), which was then classified in the following 3 categories based on the average of the rate.

Very Good: from 12 to 15
Good: from 8 to less than 12
Poor: from 0 to less than 8

The results are shown in Table 7.

The results shown in Table 7 show that the compositions according to Examples 8-11 have smoother feeling of use than Comparative Examples 12 and 13, which means that the compositions according to the present invention can provide better feeling of use.

As a result, it is clear from Table 7 that the compositions according to the present invention can provide both long-lasting matte effects and good feeling of use.

It should be noted that the compositions according to Examples 9 and 10 can show further better results as compared to the composition according to Example 8. This shows that a combination of an oil-absorbable organic particle with an oil-absorbing capacity of 170 ml/100 g and another oil-absorbable particle with an oil-absorbing capacity of 140 ml/100 g or more can provide very excellent matte and sensorial effects.

Example 12 and Comparative Examples 14-16

The following compositions in the form of a W/O emulsion according to Example 12 and Comparative Examples 14-16, shown in Table 8, were prepared by mixing the ingredients shown in Table 8 at room temperature. The numerical values for the amounts of the ingredients shown in Table 8 are all based on "% by weight" as active raw materials.

TABLE 8

| | Ex. 12 | Comp. Ex. 14 | Comp. Ex. 15 | Comp. Ex. 16 |
|---|---|---|---|---|
| Dimethicone | 15.30 | 15.30 | 15.30 | 15.30 |
| Dimethicone - PEG/PPG-18/8 Dimethicone | 2.00 | 2.00 | 2.00 | 2.00 |
| PEG-10 Dimethicone | 1.00 | 1.00 | 1.00 | 1.00 |
| Dimethicone - Dimethicone Crosspolymer | 10.00 | 10.00 | 10.00 | 10.00 |
| Dimethicone - Dimethiconol | 2.00 | 2.00 | 2.00 | 2.00 |
| Tribehenin | 1.00 | 1.00 | 1.00 | 1.00 |

TABLE 8-continued

|  | Ex. 12 | Comp. Ex. 14 | Comp. Ex. 15 | Comp. Ex. 16 |
|---|---|---|---|---|
| Isononyl Isononanoate | 5.5 | 5.5 | 5.5 | 5.5 |
| Ethylhexyl Methoxycinnamate | 7.5 | 7.5 | 7.5 | 7.5 |
| Iron oxides - Mica | 0.04 | 0.04 | 0.04 | 0.04 |
| Titanium Dioxide - Mica | 2.46 | 2.46 | 2.46 | 2.46 |
| Silica Silylate | 0.20 | 0.20 | 0.20 | 0.20 |
| Vinyl Dimethicone/Methicone Silsesquioxane | 4.00 | 4.00 | 4.00 | 4.00 |
| Porous Polylactic Acid Particle (PLA-2, Porous block) (9 μm)* (380 ml/100 g)** | 2.00 | — | — | — |
| Porous Polylactic Acid Particle (PLA-1, Porous sphere) (30 μm)* (150 ml/100 g)** | — | 2.00 | — | — |
| PMMA (10 μm)* (120 ml/100 g)** | — | — | 2.00 | — |
| Silica (3 μm)* (370 ml/100 g)** | — | — | — | 2.00 |
| Boron Nitride | 3.00 | 3.00 | 3.00 | 3.00 |
| Water | qsp 100 | qsp 100 | qsp 100 | qsp 100 |
| Glycerin | 3.00 | 3.00 | 3.00 | 3.00 |
| Butylene Glycol | 2.00 | 2.00 | 2.00 | 2.00 |
| Caprylyl Glycol | 0.50 | 0.50 | 0.50 | 0.50 |
| Phenoxyethanol | 0.50 | 0.50 | 0.50 | 0.50 |
| Magnesium Sulfate | 0.70 | 0.70 | 0.70 | 0.70 |
| Ethanol | 4.00 | 4.00 | 4.00 | 4.00 |
| Average Oil* Absorption Capacity of Powder Ingredients (ml/100 g) | 213.5 | 163.5 | 157.0 | 179.0 |
| Optical Matteness | Very Good | Good | Fair | Good |
| Lasting of Immediate Matte Effects | Very Good | Good | Fair | Fair |
| Application Smoothness | Good | Fair | Fair | Poor |

*average particle size
**oil absorption capacity based on isononyl isononanoate

[Evaluations]

The compositions according to Example 12 and Comparative Examples 14-16 were evaluated as follows.

(Sensory Tests)

25 panelists evaluated "application smoothness" after the use of the same amount of each of the compositions according to Example 12 and Comparative Examples 14-16.

Each panelist took each composition in their hands, then applied it on their faces to evaluate "optical matteness", "lasting of immediate matte effects", and "application smoothness" after the use of each composition, and rated it from 0 (low) to 15 (high), which was then classified in the following 3 categories based on the average of the rate.

Very Good: from 12 to 15

Good: from 8 to less than 12

Poor: from 0 to less than 8

The results are shown in Table 8.

As a result, it is clear from Table 8 that the compositions according to the present invention can provide both excellent matte effects and good feeling of use.

Example 13 and Comparative Example 17

The following compositions in the form of a W/O emulsion according to Example 13 and Comparative Example 17, shown in Table 9, were prepared by mixing the ingredients shown in Table 9 at room temperature. The numerical values for the amounts of the ingredients shown in Table 9 are all based on "% by weight" as active raw materials.

TABLE 9

|  | Ex. 13 | Comp. Ex. 17 |
|---|---|---|
| PEG-10 Dimethicone | 3.0 | 3.0 |
| Bis-PEG/PPG-14/14 Dimethicone (and) Dimethicone | 1.00 | 1.00 |
| Dimethicone | 20.7 | 20.7 |
| Isododecane | 10.0 | 10.0 |
| Ethylhexyl Methoxycinnamate | 7.0 | 7.0 |
| Tocopherol | 0.1 | 0.1 |
| Trimethylsiloxysilicate | 5.0 | 5.0 |
| Disteardimonium Hectorite | 0.5 | 0.5 |
| Porous Polylactic Acid Particle (Toraypearl ® PLA, Toray Industries Inc.) (11 μm)* (465.9 ml/100 g)** | 3.00 | — |
| Water | qsp 100 | qsp 100 |
| Butylene Glycol | 5.0 | 5.0 |
| Magnesium Sulfate | 0.7 | 0.7 |
| Ethanol | 12.0 | 12.0 |
| Matteness ($T_{3h} - T_{imm}$) | 4.37 ± 1.64 | 5.36 ± 2.33 |

*average particle size
**oil absorption capacity based on isononyl isononanoate

[Evaluations]

The compositions according to Example 13 and Comparative Example 17 were evaluated as follows.

(Matteness)

Each of the compositions according to Example 13 and Comparative Example 17 was applied on a contrast card as a layer with a thickness of 50 μm, and was dried for 24 hours at room temperature.

On the above layer, a powder foundation was applied such that the layer of the powder foundation was 50 μm. The composition of the powder foundation used was the same for Example 13 and Comparative Example 17.

The reflectance on the above layer just after ($T_{imm}$) and 3 hours after ($T_{3h}$) the application of the powder foundation was measured with a goniophotometer (GP-5, Murakami) as a 45° gloss value.

The difference between $T_{imm}$ and $T_{3h}$ was determined. The results are shown in Table 9.

The results shown in Table 9 show that the composition according to the present invention (Example 13) can provide higher matteness than the compositions according to Comparative Example 17, which means that the present invention can provide longer-lasting matte effects, even if the composition according to the present invention is used as a makeup base.

Examples 14 and 15, and Comparative Examples 18 and 19

The following compositions in the form of a serum according to Examples 14 and 15, and Comparative Examples 18 and 19, shown in Table 10, were prepared by mixing the ingredients shown in Table 10 at room temperature. The numerical values for the amounts of the ingredients shown in Table 10 are all based on "% by weight" as active raw materials.

TABLE 10

|  | Ex. 14 | Ex. 15 | Comp. Ex. 18 | Comp. Ex. 19 |
|---|---|---|---|---|
| Porous Polylactic Acid Particle (Toraypearl ® PLA, Toray Industries Inc.) (465.9 ml/100 g)* (11 μm)** | 2.00 | 1.00 | — | — |
| Boron Nitride | — | 1.00 | 1.00 | — |
| HDI/Trimethylol hexyllactone crosspolymer | — | — | 1.00 | — |

TABLE 10-continued

|  | Ex. 14 | Ex. 15 | Comp. Ex. 18 | Comp. Ex. 19 |
|---|---|---|---|---|
| Water | qsp100 | qsp100 | qsp100 | qsp100 |
| Glycerin | 6.86 | 6.86 | 6.86 | 6.86 |
| Phenoxyethanol | 0.49 | 0.49 | 0.49 | 0.49 |
| Propylene Glycol | 9.80 | 9.80 | 9.80 | 9.80 |
| Tetrasodium EDTA | 0.01 | 0.01 | 0.01 | 0.01 |
| Caprylyl Glycol | 0.29 | 0.29 | 0.29 | 0.29 |
| Plant Extracts | 2.26 | 2.26 | 2.26 | 2.26 |
| Salicylic acid | 0.20 | 0.20 | 0.20 | 0.20 |
| Methyl Gluceth-20 | 2.94 | 2.94 | 2.94 | 2.94 |
| PPG-5 Cetech-20 | 0.02 | 0.02 | 0.02 | 0.02 |
| Ellagic Acid | 0.49 | 0.49 | 0.49 | 0.49 |
| Dimethicone | 2.45 | 2.45 | 2.45 | 2.45 |
| Xanthan Gum | 0.15 | 0.15 | 0.15 | 0.15 |
| Acrylates/C10-30 Alkyl Acrylate Crosspolymer | 0.20 | 0.20 | 0.20 | 0.20 |
| Glyceryl Stearate (and) PEG-100 Stearate | 1.42 | 1.42 | 1.42 | 1.42 |
| Stearic Acid | 1.18 | 1.18 | 1.18 | 1.18 |
| Cetyl Alcohol | 0.74 | 0.74 | 0.74 | 0.74 |
| Diisopropyl Sebacate | 4.41 | 4.41 | 4.41 | 4.41 |
| Octyldodecanol | 1.96 | 1.96 | 1.96 | 1.96 |
| Tocopherol | 0.10 | 0.10 | 0.10 | 0.10 |
| Fragrance | 0.15 | 0.15 | 0.15 | 0.15 |
| Potassium Hydroxide | 0.95 | 0.95 | 0.95 | 0.95 |
| Ascorbyl Glucoside | 1.96 | 1.96 | 1.96 | 1.96 |
| Citric Acid | 0.05 | 0.05 | 0.05 | 0.05 |
| Sodium Citrate | 0.10 | 0.10 | 0.10 | 0.10 |
| Polyacrylamide (and) C13-14 Isoparaffin (and) Laureth-7 | 0.78 | 0.78 | 0.78 | 0.78 |
| Powder | 2.00 | 2.00 | 2.00 | 2.00 |
| Average Oil* Absorption Capacity of Powder Ingredients (ml/100 g) | 465.9 | 280.0 | 91.0 | 0 |
| In-vitro Anti-Shine Index | Good | Good | Poor | 0 |

*oil absorption capacity based on isononyl isononanoate
**average particle size

[Evaluations]

The compositions according to Examples 14 and 15, and Comparative Examples 18 and 19 were evaluated as follows.

(In-Vitro Anti-Shine Index)

Each of the compositions according to Examples 14 and 13, and Comparative Examples 18 and 19 was applied on a contrast card as a layer with a thickness of 100 μm, and was dried for 24 hours at room temperature.

An artificial sebum/sweat composition with the formulation shown in the above Table 5 was sprayed on the above layer on the contrast card, at room temperature.

The reflectance on the above layer 9 minutes after the spraying of the artificial sebum/sweat composition thereon was measured with a glossmeter (GM-268, Konika Minolta) as a 60° gloss value. The amount of the artificial sebum/sweat composition sprayed on each of the above layers was the same as each other.

The anti-shine index was calculated by the following equation:

Anti-Shine Index=(Reflectance of a sample 9 minutes after the spraying)−(Reflectance of a negative control)/(Reflectance of a positive control 9 minutes after the spraying)−(Reflectance of a negative control)

As the negative control, the composition according to Comparative Example 19 was used. As the positive control, the composition according to Comparative Example 19 with the addition of silica silylate (aerogel) in an amount of 2% by weight relative to the total weight of the composition (the amount of water was reduced by 2% by weight) was used.

The determined anti-shine index was categorized as follows.
Good (long-lasting anti-shine effect): more than 70
Poor (short-lasting anti-shine effect): 70 or less
The results are shown in Table 10.

The results shown in Table 10 show that the compositions according to the present invention (Examples 14 and 15) have better anti-shine index than the compositions according to Comparative Examples 18 and 19, which means that the matte effects by the present invention are more resistant to sebum and/or sweat.

Examples 16 and 17

The following compositions in the form of an O/W emulsion according to Examples 16 and 17, shown in Table 11, were prepared by mixing the ingredients shown in Table 11 at room temperature. The numerical values for the amounts of the ingredients shown in Table 11 are all based on "% by weight" as active raw materials.

TABLE 11

|  | Ex. 16 | Ex. 17 |
|---|---|---|
| Porous Polylactic Acid Particle (Toraypearl ® PLA, Toray Industries Inc.) (11 μm)* (465.9 ml/100 g)** | 2.00 | 1.00 |
| Silica Silylate | — | 1.00 |
| Water | qsp 100 | qsp 100 |
| Adenosine | 0.04 | 0.04 |
| Phenoxyethanol | 0.50 | 0.50 |
| Glycerin | 1.50 | 1.50 |
| Propylene Glycol | 3.00 | 3.00 |
| Disodium EDTA | 0.05 | 0.05 |
| Styrene/Acrylates Copolymer | 0.50 | 0.50 |
| Dextrin Palmitate | 0.25 | 0.25 |
| Cetyl Alcohol | 0.50 | 0.50 |
| Stearic Acid | 1.00 | 1.00 |
| Ceteth-10 | 0.40 | 0.40 |
| Isopropyl Lauroyl Sarcosinate | 5.00 | 5.00 |
| Drometrizole Trisiloxane | 1.00 | 1.00 |
| Bis-Ethylhexyloxyphenol Methoxyphenyl Triazine | 3.00 | 3.00 |
| Dimethylamino Hydroxybenzoyl Hexyl Benzoate | 3.00 | 3.00 |
| Diisopropyl Sebacate | 7.00 | 7.00 |
| Ethylhexyl Triazone | 5.00 | 5.00 |
| Titanium Dioxide (and) Aluminum Hydroxide (and) Stearic Acid | 2.50 | 2.50 |
| Caprylyl Glycol | 0.30 | 0.30 |
| Acrylate/C10-30 Alkyl Acrylate Crosspolymer | 0.25 | 0.25 |
| Potassium Hydroxide | 0.21 | 0.21 |
| Tocopheryl Acetate | 0.20 | 0.20 |
| Ammonium Polyacryloyldimethyl Taurate | 0.18 | 0.18 |
| Plant Extracts | 0.55 | 0.55 |
| Ethanol | 7.00 | 7.00 |
| Fragrance | 0.40 | 0.40 |
| Average Oil** Absorption Capacity of Powder Ingredients (ml/100 g) | 300 | 650 |
| In-vitro Anti-Shine Index | Good | Good |
| Sensory Test | | |
| Application Smoothness | Good | Good |

*average particle size
**oil absorption capacity based on isononyl isononanoate

[Evaluations]

The compositions according to Examples 16 and 17 were evaluated as follows.

(In-Vitro Anti-Shine Index)

Each of the compositions according to Examples 16 and 17 was applied on a contrast card as a layer with a thickness of 100 μm, and was dried for 24 hours at room temperature.

An artificial sebum/sweat composition with the formulation shown in the above Table 5 was sprayed on the above layer on the contrast card, at room temperature.

The reflectance on the above layer 9 minutes after the spraying of the artificial sebum/sweat composition thereon was measured with a glossmeter (GM-268, Konika Minolta) as a 60° gloss value. The amount of the artificial sebum/sweat composition sprayed on each of the above layers was the same as each other.

The anti-shine index was calculated by the following equation:

Anti-Shine Index=(Reflectance of a sample 9 minutes after the spraying)−(Reflectance of a negative control)/(Reflectance of a positive control 9 minutes after the spraying)−(Reflectance of a negative control)

As the negative control, the composition according to Example 16 without the porous polylactic acid particle was used. As the positive control, the composition according to Example 16 with the addition of silica sylylate (aerogel) in an amount of 2% by weight relative to the total weight of the composition, instead of the porous polylactic acid particle, was used.

The determined anti-shine index was categorized as follows.

Good (long-lasting anti-shine effect): more than 70
Poor (short-lasting anti-shine effect): 70 or less The results are shown in Table 11.

(Sensory Test)

25 panelists evaluated "application smoothness" after the use of the same amount of each of the compositions according to Examples 16 and 17.

Each panelist took each composition in their hands, then applied it on their faces to evaluate "application smoothness" after the use of each composition, and rated it from 0 (low) to 15 (high), which was then classified in the following 3 categories based on the average of the rate.

Very Good: from 12 to 15
Good: from 8 to less than 12
Poor: from 0 to less than 8

The results are shown in Table 11.

As a result, it is clear from Table 11 that the compositions according to the present invention can provide both excellent matte effects and good feeling of use.

The invention claimed is:

1. A cosmetic makeup composition in the form of an emulsion, comprising:
   (a) at least one porous oil-absorbable polylactic acid particle which has an oil-absorbing capacity of 180 ml/100 g or more, a volume-average particle size of less than 30 μm, and a density ranging from 0.01 g/cm$^3$ to 0.9 g/cm$^3$;
   (b) at least one oil;
   (c) at least one emulsifier; and
   (d) water;
      wherein the (a) at least one porous oil-absorbable polylactic acid particle is present in an amount of from 0.1% to 10% by weight relative to the total weight of the composition.

2. The composition according to claim 1, wherein the at least one porous oil-absorbable polylactic acid particle has an oil-absorbing capacity of 350 ml/100 g or more.

3. The composition according to claim 1, wherein the at least one porous oil-absorbable polylactic acid particle has a volume-average particle size of from 8 to less than 12 μm.

4. The composition according to claim 1, wherein the amount of the (c) at least one emulsifier in the composition is from 0.01 to 20% by weight, relative to the total weight of the composition.

5. The composition according to claim 1, wherein the amount of the (d) water in the composition is from 1 to 99% by weight, relative to the total weight of the composition.

6. A cosmetic makeup composition, in the form of an emulsion, comprising:
   (a) at least one porous oil-absorbable polylactic acid particle which has an oil absorbing capacity of 180 ml/100 g or more, a volume-average particle size of less than 30 μm, and a density ranging from 0.01 g/cm$^3$ to 0.9 g/cm$^3$;
   (b) at least one oil;
   (c) at least one emulsifier;
   (d) water; and
   (e) at least one additional oil-absorbable particle;
      wherein the (a) at least one porous oil-absorbable polylactic acid particle is present in an amount of from 0.1% to 10% by weight relative to the total weight of the composition, and
      wherein the (e) at least one additional oil-absorbable particle is present in an amount sufficient to provide a total oil-absorbing capacity of the (a) at least one porous oil-absorbable polylactic acid particle and the (e) at least one additional oil-absorbable particle in the composition of more than 170 ml/100 g.

7. The composition according to claim 6, wherein the (e) at least one additional oil-absorbable particle comprises at least one material selected from the group consisting of cellulose, silica, silicate, perlite, boron nitride, magnesium carbonate, magnesium hydroxide, hydrophobic silica, kaolin, talc, polyamide powders, powders of acrylic polymers, polymethyl methacrylate, of polymethyl methacrylate/ethylene glycol di methacrylate, of polyallyl methacrylate/ethylene glycol dimethacrylate, or of ethylene glycol dimethacrylate/lauryl methacrylate copolymer, silicones, or mixtures thereof.

8. The composition according to claim 6, wherein the (e) at least one additional oil-absorbable particle has an oil-absorbing capacity of 140 ml/100 g or more.

9. The composition according to claim 6, wherein the (e) at least one additional oil-absorbable particle has an oil-absorbing capacity of 350 ml/100 g or more.

10. The composition according to claim 6, wherein the oil-absorbing capacity of the total of the (a) at least one porous oil-absorbable organic particle and the (e) at least one additional oil-absorbable particle in the composition is more than 200 ml/100 g.

11. The composition according to claim 6, wherein the oil-absorbing capacity of the total of the (a) at least one porous oil-absorbable polylactic acid particle and the (e) at least one additional oil-absorbable particle in the composition is more than 250 ml/100 g.

12. The composition according to claim 1, wherein the composition further comprises at least one ingredient selected from the group consisting of polyols, thickeners, preservatives, co-preservatives, or mixtures thereof.

13. A cosmetic process for a keratin substance, comprising applying to the keratin substance the composition according to claim 1.

14. The composition according to claim 1, wherein the amount of the (b) at least one oil in the composition is from 20% to 80% by weight relative to the total weight of the composition.

15. The composition according to claim 1, wherein the at least one oil is chosen from hydrocarbon oils, ester oils, silicone oils, synthetic oils, or mixtures thereof.

16. The composition according to claim 6, wherein the at least one oil is chosen from hydrocarbon oils, ester oils, silicone oils, synthetic oils, or mixtures thereof.

17. The composition according to claim 1, wherein the at least one porous oil-absorbable polylactic acid particle comprises at least one organic material derived from plants.

18. The composition according to claim 6, wherein the at least one porous oil-absorbable polylactic acid particle comprises at least one organic material derived from plants.

19. A cosmetic makeup composition in the form of an emulsion, comprising:
  (a) from 0.1% to 10% by weight, relative to the weight of the composition, of at least one porous oil-absorbable polylactic acid particle which has an oil-absorbing capacity of 300 ml/100 g or more, and a volume-average particle size ranging from 5 to less than 20 µm;
  (b) at least one oil chosen from hydrocarbon oils, ester oils, silicone oils, synthetic oils, or mixtures thereof;
  (c) at least one emulsifier chosen from anionic surfactants, non-ionic surfactants, amphoteric surfactants, zwitterionic surfactants, or mixtures thereof;
  (d) water; and
  (e) at least one additional component chosen from anionic polymers, cationic polymers, nonionic polymers, amphoteric polymers, UV filters, sunscreen agents, thickening agents, organic solvents, additional oil-absorbable particles, vitamins, suspending agents, stabilizers, dyes, or mixtures thereof.

20. The composition according to claim 19, comprising from 1% to 5% by weight, relative to the weight of the composition, of at least one porous oil-absorbable polylactic acid particle which has an oil-absorbing capacity ranging from 300 ml/100 g to 800 ml/100 g, a volume-average particle size ranging from 8 to less than 12 µm, and a density ranging from 0.01 g/cm$^3$ to 0.9 g/cm$^3$.

\* \* \* \* \*